(12) United States Patent
Borkowski

(10) Patent No.: US 8,007,807 B2
(45) Date of Patent: Aug. 30, 2011

(54) MULTIPLE VACCINATION INCLUDING SEROGROUP C MENINGOCOCCUS

(75) Inventor: Astrid Borkowski, Marburg (DE)

(73) Assignee: Novartis Vaccines and Diagnostics GmbH, Marburg (DE)

( * ) Notice: Subject to any disclaimer, the term of this patent is extended or adjusted under 35 U.S.C. 154(b) by 261 days.

(21) Appl. No.: 11/991,438

(22) PCT Filed: Sep. 1, 2006

(86) PCT No.: PCT/IB2006/002861
§ 371 (c)(1),
(2), (4) Date: Jan. 8, 2009

(87) PCT Pub. No.: WO2007/026249
PCT Pub. Date: Mar. 8, 2007

(65) Prior Publication Data
US 2010/0034847 A1   Feb. 11, 2010

Related U.S. Application Data

(60) Provisional application No. 60/713,801, filed on Sep. 1, 2005, provisional application No. 60/750,894, filed on Dec. 16, 2005.

(51) Int. Cl.
*A61K 39/00* (2006.01)
*A61K 39/02* (2006.01)
*A61K 39/385* (2006.01)
*C07K 1/00* (2006.01)

(52) U.S. Cl. ............. 424/184.1; 424/193.1; 424/197.11; 424/234.1; 424/236.1; 530/350

(58) Field of Classification Search .................. None
See application file for complete search history.

(56) References Cited

U.S. PATENT DOCUMENTS

2003/0180316 A1* 9/2003 Boutriau et al. ........... 424/190.1

FOREIGN PATENT DOCUMENTS

| WO | WO 02/00249 | 1/2002 |
|---|---|---|
| WO | WO 02/080965 | 10/2002 |
| WO | WO 2005/004909 | 1/2005 |
| WO | WO 2006/113528 | 10/2006 |
| WO | WO 2007/000314 | 1/2007 |
| WO | WO 2007/000332 | 1/2007 |

OTHER PUBLICATIONS

Halperin, S. et al. "Simultaneous administration of meningococcal C conjugate vaccine and diphtheria-tetanus-acellular pertussis . . . " Clin Invest Med, 25(6): 243-251 (2002).
Slack, M. et al. "Immune response of premature infants to meningococcal serogroup C and combined diphtheria-tetanus toxoids-acellular . . . " JID, 184(12): 1617-1620 (2001).
Buttery, J. et al. "Immunogenicity and safety of a combination pneumococcal-meningococcal vaccine in infants" JAMA, 293(14): 1751-1758 (2005).
Eskola, J. et al. "Reactogenicity and immunogenicity of combined vaccines for bacteraemic diseases caused by Haemophilus influenzae type b . . . " VACCINE, 8(2): 107-110 (1990).
Rennels, M. et al. "Safety and immunogenicity of combined conjugate 9-valent S. pneumoniae-meningococcal group C . . . " 41st ICAAC Abstracts, 41: 283 (2001).
Tejedor, J. et al. "Immunogenicity and reactogenicity of a three-dose primary vaccination course with a . . . " The Pediatric Infectious Disease Journal, 23(12): 1109-1115 (2004).
Tejedor, J. et al. "Immunogenicity and reactogenicity of primary immunization with a hexavalent diphtheria . . . " The Pediatric Infectious Disease Journal, 25(8): 713-720 (2006).
Kitchin, N. et al. "Evaluation of a diphtheria-tetanus-acellular pertussis-inactivated poliovirus-Haemophilus . . . " Archives of Disease in Childhood, 92(1): 11-16 (2007).
Tejedor, J. et al. "Immunogenicity and reactogenicity of primary immunization with a novel combined Haemophilus . . . " The Pediatric Infectious Disease Journal, 26(1): 1-7 (2007).
Tejedor, J. et al. "Antibody persistence after primary vaccination with a hexavalent DTPa-HBV-IPV . . . " The Pediatric Infectious Disease Journal, 25(10): 943-945 (2006).

* cited by examiner

*Primary Examiner* — Albert Navarro
(74) *Attorney, Agent, or Firm* — Helen Lee; Otis Littlefield

(57) ABSTRACT

Various improvements to vaccines that include a serogroup C meningococcal conjugate antigen, including: (a) co-administration with acellular *B. pertussis* antigen; (b) co-administration with an inactivated poliovirus antigen; (c) supply in a kit together with a separate pneumococcal conjugate component, which may be in a liquid form; and (d) use in combination with a pneumococcal conjugate antigen but without an aluminum phosphate adjuvant. A kit may have: (a) a first immunogenic component that comprises an aqueous formulation of a conjugated capsular saccharide from *Streptococcus pneumoniae*; (b) a second immunogenic component that comprises a conjugated capsular saccharide from *Neisseria meningitidis* serogroup C.

40 Claims, No Drawings

MULTIPLE VACCINATION INCLUDING SEROGROUP C MENINGOCOCCUS

RELATED APPLICATIONS

This application is the U.S. National Phase of International Application No. PCT/IB2006/002861, filed Sep. 1, 2006 and published in English, which claims priority to U.S. Provisional Application No. 60/713,801, filed Sep. 1, 2005 and U.S. Provisional Application No. 60/750,894, filed Dec. 16, 2005. The teachings of the above applications are incorporated herein in their entirety by reference.

All documents cited herein are incorporated by reference in their entirety.

TECHNICAL FIELD

This invention is in the field of immunising patients against multiple pathogens.

BACKGROUND ART

Vaccines containing antigens from more than one pathogenic organism within a single dose are known as "multivalent" or "combination" vaccines. Various combination vaccines have been approved for human use in the EU and the USA, including trivalent vaccines for protecting against diphtheria, tetanus and pertussis ("DTP" vaccines) and trivalent vaccines for protecting against measles, mumps and rubella ("MMR" vaccines).

Combination vaccines offer patients the advantage of receiving a reduced number of injections, which leads to the clinical advantage of increased compliance (e.g. see chapter 29 of reference 1), particularly for pediatric vaccination. At the same time, however, they present manufacturing difficulties due to factors including: physical and biochemical incompatibility between antigens and other components; immunological interference; and stability. Various combination vaccines are disclosed in references 2 to 10.

In 2005, a widely-publicised study [11] reported that the immunogenicity of N. meningitidis serogroup C ('MenC') capsular saccharide conjugate vaccine was diminished when it was administered with a 9-valent S. pneumoniae conjugated saccharide as a combination vaccine. Moreover, diminished responses were seen to both co-administered H. influenzae type b ('Hib') conjugate and co-administered diphtheria toxoid. The authors concluded that the 'Pnc9-MenC' combination vaccine "may not be a suitable replacement for individual MenC or pneumococcal glycoconjugate vaccines". Moreover, they suggested that the incompatibility may not be linked to the combined nature of the antigens, and that it is "possible that the administration of the vaccines separately may have had the same effect".

Thus there remains a need for an immunisation that can protect against MenC and *pneumococcus* without significant loss of immunogenicity of these two components. There is an additional need for an immunisation that can protect against MenC, *pneumococcus*, diphtheria and Hib without significant loss of immunogenicity of these four components. More generally, there remains a need for integrating MenC immunisation into existing immunisation schedules.

DISCLOSURE OF THE INVENTION

Whereas the reference 11 study found a reduction in MenC immunogenicity, this reduction is not seen with the present invention. Compared to the reference 11 study, the invention differs in several key aspects, which can be exploited individually or in combination to achieve success in place of the prior art's failure.

Whereas the reference 11 study used a whole-cell B. pertussis antigen, and found a reduction in MenC immunogenicity, in a first aspect of the invention a MenC conjugate antigen is co-administered with acellular B. pertussis antigen(s), and no loss of immunogenicity has been observed. This situation contrasts with previous experience with Hib conjugates, which are generally compatible with whole cell pertussis but which have often been reported to be incompatible with acellular pertussis. It also contrasts with previous experience with pneumococcal conjugates, where antibody responses were reduced when co-administered with acellular B. pertussis antigen(s) but were not reduced if a cellular antigen was used [2]. The use of acellular antigens, rather than cellular, offers advantages in terms of safety and reactogenicity.

Moreover, whereas the reference 11 study administered the MenC/Pnc9 vaccine at the same time as an oral polio vaccine ('OPV'), and found a reduction in MenC immunogenicity, in a second aspect of the invention a MenC conjugate antigen is co-administered with a polio vaccine in injectable form, such as in inactivated poliovirus vaccine ('IPV'), and no loss of immunogenicity has been observed. The use of IPV instead of OPV eliminates the risk of vaccine-associated polio paralysis.

In addition, whereas the reference 11 study used a vaccine composition in which pneumococcal and MenC conjugates were supplied as a pre-mixed combination, and found a reduction in MenC immunogenicity, in a third aspect of the invention a MenC conjugate antigen is supplied separately from the pneumococcal conjugates, in the form of a kit of parts, and no loss of immunogenicity has been observed. The MenC and pneumococcal conjugates can be administered to a patient separately (e.g. at different sites), or they can be mixed at the time of use for combined administration. Manufacturing and distributing a kit is less convenient that for a full-liquid combination vaccine, but this sort of kit is currently in use (e.g. in the INFANRIX HEXA™ product) and the inconvenience can be more than offset by the increased immunogenicity and stability of the antigens.

Furthermore, whereas the reference 11 study used a vaccine composition in which pneumococcal and MenC conjugates were supplied as a lyophilised combination, and found a reduction in MenC immunogenicity, in a fourth aspect of the invention a pneumococcal conjugate antigen is supplied in a liquid form, and no loss of immunogenicity has been observed. The MenC conjugate may be in lyophilised form, or may also be in liquid form. Supplying the pneumococcal conjugate in liquid form avoids the need for its reconstitution at the time of use, and also allows it to be used to reconstitute any other immunogenic components that are in lyophilised form.

Additionally, whereas the reference 11 study used a vaccine composition in which pneumococcal and MenC conjugates were supplied in combination with an aluminium phosphate adjuvant, and found a reduction in MenC immunogenicity, in a fifth aspect of the invention a meningococcal conjugate antigen is supplied without an aluminium phosphate adjuvant, and no loss of immunogenicity has been observed. The aluminium phosphate adjuvant can be replaced with an aluminium hydroxide adjuvant, or it is possible to include no aluminium adjuvant at all. Further alternative arrangements of aluminium salts are also possible.

Finally, in a sixth aspect of the invention MenC and a pneumococcal conjugate are administered with either or both of an acellular pertussis antigen and an inactivated poliovirus antigen, and the two conjugates use the same carrier protein. Using a common carrier protein reduces the overall number of different antigens that are simultaneously presented to the immune system, and also offers more convenience during manufacture. If more than one pneumococcal conjugate is administered then each pneumococcal conjugate may have the same carrier protein, or there may be different carrier proteins, but at least one of the pneumococcal conjugates will have the same carrier protein as the MenC conjugate.

These six aspects of the invention are described in more detail below.

Reference 3, published in December 2004, describes a study in which the INFANRIX HEXA™ (GSK) was co-administered to infants, into separate thighs, with MENING-ITEC™ (Wyeth). INFANRIX HEXA™ is supplied as a liquid D-T-Pa-HBsAg-IPV formulation with an additional lyophilised Hib component, and the Hib component is resuspended with the 5-valent liquid formulation at the time of use to give a 6-valent combination vaccine. MENINGITEC™ is supplied as a liquid formulation containing an aluminium phosphate adjuvant. In contrast, with the fifth aspect of the present invention a meningococcal conjugate antigen is supplied without an aluminium phosphate adjuvant. Also in contrast to reference 3, in a seventh aspect of the invention a meningococcal conjugate antigen is supplied in a lyophilised form. This lyophilised form will be reconstituted into aqueous form prior to injection, and the reconstitution may use (a) an aqueous D-T-Pa-containing formulation, to give a combination vaccine or (b) a separate aqueous carrier, for co-administration with a D-T-Pa-containing formulation.

Reference 4 discloses a study in which a meningococcal C conjugate vaccine was co-administered with a 5-valent D-T-Pa-IPV-Hib vaccine. Reference 5 discloses a study in which a pneumococcal C conjugate vaccine was co-administered with a 5-valent D-T-Pa-IPV-Hib vaccine. Neither of these 5-valent vaccines included a HBsAg component. Reference 6 discloses studies in which (a) HBsAg was administered at the same time as a pneumococcal conjugate vaccine in infants, and (b) separate D-T-Pa and Hib vaccines were administered at the same time as a pneumococcal conjugate vaccine in toddlers. Reference 7 describes a study in which a meningococcal C conjugate vaccine was co-administered with a 4-valent D-T-Pa-Hib vaccine. In an eighth aspect of the invention, meningococcal serogroup C and pneumococcal conjugates are administered with a hepatitis B surface antigen. In a ninth aspect of the invention, meningococcal serogroup C and pneumococcal conjugates are administered with an inactivated poliovirus antigen.

These nine aspects of the invention are described in more detail below. The nine aspects can be exploited individually or in combination.

Reference 8 describes a study in which a 6-valent D-T-Pa-HBV-IPV-Hib vaccine was co-administered with a 7-valent pneumococcal conjugate vaccine, but no meningococcal conjugates were used. References 9 and 10 describe various possible combination vaccines, which may include meningococcal conjugates, but specific details are lacking e.g. there is no disclosure of the O-acetylation status of the proposed meningococcal serogroup C saccharides.

Use of Acellular *pertussis* Antigen(s)

In a first aspect of the invention, a MenC conjugate ('MCC') antigen is co-administered with acellular *B. pertussis* antigen(s), usually known as 'Pa'. The MCC and the Pa antigens may be administered to a patient separately, or they may be administered as a combination vaccine.

Thus the invention provides a kit, comprising a first immunogenic component and a second immunogenic component, wherein: (a) the first immunogenic component comprises a conjugated capsular saccharide from *N. meningitidis* serogroup C; and (b) the second immunogenic component comprises an acellular *B. pertussis* antigen.

In addition to acellular *B. pertussis* antigens, the second immunogenic component preferably includes one or more of: a diphtheria toxoid; a tetanus toxoid; a HBsAg; an inactivated poliovirus antigen; and, optionally, a conjugated Hib antigen.

The kit may also include a component including a conjugated pneumococcal saccharide antigen.

The invention also provides an immunogenic composition comprising: (a) a conjugated capsular saccharide from *N. meningitidis* serogroup C; and (b) an acellular *B. pertussis* antigen. In addition to the MCC and acellular *B. pertussis* antigens, the composition may include one or more of: a diphtheria toxoid; a tetanus toxoid; a HBsAg; an inactivated poliovirus antigen; and, optionally, a conjugated Hib antigen. It may also include a conjugated pneumococcal saccharide antigen.

Use of an Injectable Polio Vaccine

In a second aspect of the invention, a MenC conjugate ('MCC') antigen is co-administered with an injectable poliovirus antigen, such as the inactivated polio vaccine ('IPV'), also known as the Salk vaccine. The MCC and the IPV antigens may be administered to a patient separately, or they may be administered as a combination vaccine.

Thus the invention provides a kit, comprising a first immunogenic component and a second immunogenic component, wherein: (a) the first immunogenic component comprises a conjugated capsular saccharide from *N. meningitidis* serogroup C; and (b) the second immunogenic component comprises an inactivated poliovirus antigen.

In addition to IPV, the second immunogenic component preferably includes one or more of: a diphtheria toxoid; a tetanus toxoid; a HBsAg; an acellular pertussis antigen; and, optionally, a conjugated Hib antigen.

The kit may also include a component including a conjugated pneumococcal saccharide antigen.

The invention also provides an immunogenic composition comprising: (a) a conjugated capsular saccharide from *N. meningitidis* serogroup C; and (b) an inactivated poliovirus antigen. In addition to the MCC and acellular *B. pertussis* antigens, the composition may include one or more of: a diphtheria toxoid; a tetanus toxoid; a HBsAg; an acellular pertussis antigen; and, optionally, a conjugated Hib antigen. It may also include a conjugated pneumococcal saccharide antigen.

Supplying MenC as a Separate Kit Component

In a third aspect of the invention, a MenC conjugate ('MCC') antigen is supplied separately from the pneumococcal conjugates ('PnC'), in the form of a kit of parts.

Thus the invention provides a kit, comprising a first immunogenic component and a second immunogenic component, wherein: (a) the first immunogenic component comprises a conjugated capsular saccharide from *N. meningitidis* serogroup C; and (b) the second immunogenic component comprises a conjugated capsular saccharide from *S. pneumoniae*.

The first component may additionally include one or more of: a diphtheria toxoid; a tetanus toxoid; a pertussis antigen; and a HBsAg. It may also include an inactivated poliovirus antigen. It may also include a conjugated Hib antigen. Where one of these six additional antigens is included in the first component, however, it will not also be included in the second component.

The second component may additionally include one or more of: a diphtheria toxoid; a tetanus toxoid; a pertussis antigen; and a HBsAg. It may also include an inactivated poliovirus antigen. It may also include a conjugated Hib antigen. Where one of these six additional antigens is included in the second component, however, it will not also be included in the first component.

Where neither the first nor the second component contains a diphtheria toxoid, the diphtheria toxoid may be included within a further component of the kit. Similarly, where neither the first nor the second component contains a tetanus toxoid, the tetanus toxoid may be included within a further component of the kit. Similarly, where neither the first nor the second component contains a pertussis antigen, the pertussis antigen may be included within a further component of the kit. Similarly, where neither the first nor the second component contains a HBsAg, the HBsAg may be included within a further component of the kit. Similarly, where neither the first nor the second component contains a Hib conjugate, the Hib conjugate may be included within a further component of the kit. Similarly, where neither the first nor the second component contains IPV, the IPV may be included within a further component of the kit.

Diphtheria, tetanus and pertussis antigens will typically be included together within the same component in the kit.

Liquid Pneumococcal Conjugates

In a fourth aspect of the invention, a pneumococcal conjugate antigen is supplied in a liquid form. A co-administered MenC conjugate may be supplied: (i) separately, in lyophilised form; (ii) separately, also in a liquid form; or (iii) in admixture with the pneumococcal conjugate, in liquid form.

Thus the invention provides a kit, comprising a first immunogenic component and a second immunogenic component, wherein: (a) the first immunogenic component comprises an aqueous formulation of a conjugated capsular saccharide from *S. pneumoniae*; and (b) the second immunogenic component comprises a conjugated capsular saccharide from *N. meningitidis* serogroup C. The MCC in the second component may be an aqueous formulation or a lyophilised formulation.

The first and/or second component may also include one or more of: a diphtheria toxoid; a tetanus toxoid; *B. pertussis* antigen(s); a HBsAg; and an inactivated poliovirus antigen. Preferably all five of these additional antigens are included in either the first component or the second component. As an alternative, the five antigens may be provided as a third immunogenic component in the kit. The kit may include a conjugated Hib antigen in the first or second (or third) component.

The invention also provides an immunogenic composition comprising a conjugated capsular saccharide from *S. pneumoniae* and a conjugated capsular saccharide from *N. meningitidis* serogroup C, wherein the composition is in aqueous form. The immunogenic composition preferably also includes one or more of: a diphtheria toxoid; a tetanus toxoid; acellular *B. pertussis* antigen(s); a HBsAg; an inactivated poliovirus antigen; and, optionally, a conjugated Hib antigen.

Aluminium Phosphate Adjuvant with MenC

In a fifth aspect of the invention, a meningococcal conjugate antigen is supplied without an aluminium phosphate adjuvant. The aluminium phosphate adjuvant can be replaced with an aluminium hydroxide adjuvant, or it is possible to include no aluminium adjuvant at all. A co-administered pneumococcal conjugate may be supplied with an aluminium phosphate adjuvant.

Thus the invention provides a kit, comprising a first immunogenic component and a second immunogenic component, wherein: (a) the first immunogenic component comprises a conjugated capsular saccharide from *N. meningitidis* serogroup C, but does not include an aluminium phosphate adjuvant; and (b) the second immunogenic component comprises a conjugated capsular saccharide from *S. pneumoniae*.

In preferred arrangements, the first immunogenic component does not include an aluminium phosphate adjuvant, but it may include an aluminium hydroxide adjuvant. As an alternative, it may include no aluminium salts, in which case it may include a non-aluminium-based adjuvant, or it may include no adjuvant at all.

In an alternative arrangement, where aluminium phosphate is permitted in the first component, the first component can include a mixture of aluminium hydroxide and phosphate adjuvants. Thus the invention also provides an immunogenic composition comprising a conjugated capsular saccharide from *N. meningitidis* serogroup C and a conjugated capsular saccharide from *S. pneumoniae*, wherein the composition includes an aluminium hydroxide adjuvant and an aluminium phosphate adjuvant.

In a further alternative arrangement, an aluminium phosphate adjuvant is permitted in the first component, and the meningococcal conjugate component is adsorbed to an aluminium phosphate adjuvant. Thus the invention also provides an immunogenic composition comprising a conjugated capsular saccharide from *N. meningitidis* serogroup C and a conjugated capsular saccharide from *S. pneumoniae*, *N. meningitidis* serogroup C conjugate is adsorbed to an aluminium phosphate adjuvant. The invention also provides a kit, comprising a first immunogenic component and a second immunogenic component, wherein: (a) the first immunogenic component comprises a conjugated capsular saccharide from *N. meningitidis* serogroup C, which is adsorbed to an aluminium phosphate adjuvant; and (b) the second immunogenic component comprises a conjugated capsular saccharide from *S. pneumoniae*. The pneumococcal conjugate may also be adsorbed to an aluminium phosphate adjuvant.

The may additionally include one or more of: a diphtheria toxoid; a tetanus toxoid; a pertussis antigen; and a HBsAg. It may also include an inactivated poliovirus antigen. It may also include a conjugated Hib antigen.

Carrier Proteins for MenC and PnC

In a sixth aspect of the invention, MenC and pneumococcal conjugates are administered with either or both of an acellular pertussis antigen and an inactivated poliovirus antigen, and the two conjugates use the same carrier protein. Despite the risks of carrier-induced suppression, it has been found herein that MenC and pneumococcal conjugates do not interfere with each other, which contrasts to the authors' suggestions in reference 11.

Thus the invention provides an immunogenic composition comprising: (a) a capsular saccharide from *S. pneumoniae*, conjugated to a first carrier protein, (b) a capsular saccharide from *N. meningitidis* serogroup C, conjugated to a second carrier protein, and (c) an acellular pertussis antigen and/or an inactivated poliovirus antigen, characterised in that the first carrier protein and the second carrier protein are the same. The composition may also include one or more of: a diphtheria toxoid; a tetanus toxoid; a HBsAg; and/or a conjugated Hib saccharide.

Using "the same" carrier protein does not mean that there is a single carrier protein molecule to which both pneumococcal and meningococcal saccharides are attached (cf. reference 12). Rather, the two conjugates are separate from each other, but the carrier used in the first conjugate is the same carrier as used in the second conjugate e.g. the pneumococcal saccharides are conjugated to CRM197, and the meningococcal saccharides are also conjugated to CRM197, but there is no CRM197 to which both pneumococcal and meningococcal saccharides are conjugated. Thus the conjugates are prepared separately and are subsequently combined.

The invention also provides kits including PnC, MCC and one or both of Pa or IPV:

a kit, comprising at least a first immunogenic component and a second immunogenic component, wherein: (a) one of the components comprises a capsular saccharide from *S. pneumoniae*, conjugated to a first carrier protein, (b) one of the components comprises a capsular saccharide from *N. meningitidis* serogroup C, conjugated to a second carrier protein, (c) one of the components comprises an acellular pertussis antigen, characterised in that the first carrier protein and the second carrier protein are the same.

a kit, comprising at least a first immunogenic component and a second immunogenic component, wherein: (a) one of the components comprises a capsular saccharide from *S. pneumoniae*, conjugated to a first carrier protein, (b) one of the components comprises a capsular saccharide from *N. meningitidis* serogroup C, conjugated to a second carrier protein, (c) one of the components comprises an inactivated poliovirus antigen, characterised in that the first carrier protein and the second carrier protein are the same.

Antigens (a), (b) and (c) are all present within the kit, but they are not all part of the same kit component. The following arrangements of antigens are possible, with up to three separate components for antigens (a), (b) and (c):

| Component 1 | (a) | (a) & (b) | (a) & (c) | (a) |
| Component 2 | (b) & (c) | (c) | (b) | (b) |
| Component 3 | — | — | — | (c) |

For providing each of PnC, MCC, Pa and IPV, the invention provides a kit, comprising at least a first immunogenic component and a second immunogenic component, wherein: (a) one of the components comprises a capsular saccharide from *S. pneumoniae*, conjugated to a first carrier protein, (b) one of the components comprises a capsular saccharide from *N. meningitidis* serogroup C, conjugated to a second carrier protein, (c) one of the components comprises an acellular pertussis antigen; and (d) one of the components comprises an inactivated poliovirus antigen, characterised in that the first carrier protein and the second carrier protein are the same.

Antigens (a), (b), (c) and (d) are all present within the kit, but they are not all part of the same kit component. The following arrangements of antigens are encompassed, with up to four separate components for antigens (a), (b), (c) and (d):

If the composition or kit includes saccharides from more than one serotype of *S. pneumoniae* and/or more than one serogroup of *N. meningitidis*, this aspect of the invention requires that the same carrier protein is used for at least one of the *S. pneumoniae* conjugates and at least one of the *N. meningitidis* conjugates. In some embodiments, the same carrier protein will be used for all of the *S. pneumoniae* conjugates and at least one of the *N. meningitidis* conjugates. In other embodiments, the same carrier protein will be used for at least one of the *S. pneumoniae* conjugates and all of the *N. meningitidis* conjugates. In other embodiments, the same carrier protein will be used for all of the *S. pneumoniae* conjugates and all of the *N. meningitidis* conjugates. Carrier choice is discussed in more detail below.

Where the composition or the kit includes a conjugated Hib saccharide then the carrier protein in the Hib saccharide may be the same as the carrier in the pneumococcal and meningococcal conjugates, or the Hib conjugate may use a different carrier.

Where the composition or the kit includes a tetanus toxoid then the carrier protein in the pneumococcal conjugate and the meningococcal conjugate is preferably not a tetanus toxoid. In some embodiments, none of the pneumococcal conjugates and meningococcal conjugates have a tetanus toxoid carrier.

Where the composition or the kit includes a diphtheria toxoid then the carrier protein in the pneumococcal conjugate and the meningococcal conjugate is preferably not a diphtheria toxoid. In some embodiments, none of the pneumococcal conjugates and meningococcal conjugates have a diphtheria toxoid carrier.

Where the composition or the kit includes both a diphtheria toxoid and a tetanus toxoid then the carrier protein in the pneumococcal and meningococcal conjugates is preferably neither a diphtheria toxoid nor a tetanus toxoid.

Lyophilisation of MenC

In a seventh aspect of the invention, a meningococcal serogroup C conjugate antigen is supplied in a lyophilised form in a kit that also includes an aqueous D-T-Pa-containing formulation.

Thus the invention provides a kit, comprising a first immunogenic component and a second immunogenic component, wherein: (a) the first immunogenic component comprises an aqueous formulation of a diphtheria toxoid, a tetanus toxoid and acellular *B. pertussis* antigen; and (b) the second immunogenic component comprises a conjugated capsular saccharide from *N. meningitidis* serogroup C, in lyophilised form.

The lyophilised MenC conjugate will be reconstituted into aqueous form prior to injection. The reconstitution step can use (a) the aqueous D-T-Pa-containing formulation, to give a

| Component 1 | (a) | (a) | (a) | (a) | (a) | (a) & (b) | (a) & (b) |
| Component 2 | (b), (c) & (d) | (b) | (b) & (c) | (b) & (d) | (b) | (c) & (d) | (c) |
| Component 3 | — | (c) & (d) | (d) | (c) | (c) | — | (d) |
| Component 4 | — | — | — | — | (d) | — | — |
| Component 1 | (a) & (c) | (a) & (c) | (a), (b) & (c) | (a), (b) & (d) | (a), (c) & (d) | (a) & (d) | (a) & (d) |
| Component 2 | (b) | (b) & (d) | (d) | (c) | (b) | (b) | (b) & (c) |
| Component 3 | (d) | — | — | — | — | (c) | — |
| Component 4 | — | — | — | — | — | — | — |

Typically, antigens (c) and (d) will be part of the same component.

These kits may also include one or more of: a diphtheria toxoid; a tetanus toxoid; a HBsAg; and/or a conjugated Hib saccharide.

combination vaccine including the MenC conjugate or (b) a separate aqueous carrier, to give a second injection for co-administration with a D-T-Pa-containing injection, in which case the kit may include an aqueous carrier as a further component.

The D-T-Pa-containing formulation may also include either or both of: a hepatitis B virus surface antigen; and an inactivated poliovirus antigen.

A conjugated Hib antigen may also be included within the kit. It may be included in lyophilised form (e.g. in the same container as the lyophilised MenC component), or within the D-T-Pa-containing formulation.

Administration of MenC, PnC and HBsAg

In an eighth aspect of the invention, meningococcal serogroup C and pneumococcal conjugates are administered with a hepatitis B surface antigen.

Thus the invention provides an immunogenic composition comprising: (a) a conjugated capsular saccharide from *S. pneumoniae*, (b) a conjugated capsular saccharide from *N. meningitidis* serogroup C, and (c) a hepatitis B virus surface antigen. The composition may also include one or more of: a diphtheria toxoid; a tetanus toxoid; a *B. pertussis* antigen; an inactivated poliovirus antigen; and/or a conjugated Hib saccharide.

The invention also provides a kit, comprising at least a first immunogenic component and a second immunogenic component, wherein: (a) one of the components comprises a conjugated capsular saccharide from *S. pneumoniae*, (b) one of the components comprises a conjugated capsular saccharide from *N. meningitidis* serogroup C, (c) one of the components comprises a hepatitis B virus surface antigen.

Antigens (a), (b) and (c) are all present within the kit, but they are not all part of the same kit component. The following arrangements of antigens are possible, with up to three separate components for antigens (a), (b) and (c):

| Component 1 | (a)       | (a) & (b) | (a) & (c) | (a) |
|-------------|-----------|-----------|-----------|-----|
| Component 2 | (b) & (c) | (c)       | (b)       | (b) |
| Component 3 | —         | —         | —         | (c) |

The kit may also include one or more of: a diphtheria toxoid; a tetanus toxoid; a *B. pertussis* antigen; an inactivated poliovirus antigen; and/or a conjugated Hib saccharide. These additional antigens may be included within the same kit component as any of (a), (b) or (c), or may be in separate component(s). Typically, however, a single kit component can include all of: a HBsAg; a diphtheria toxoid; a tetanus toxoid; a *B. pertussis* antigen; and an inactivated poliovirus antigen.

Administration of MenC, PnC and IPV

In a ninth aspect of the invention, meningococcal serogroup C and pneumococcal conjugates are administered with an inactivated poliovirus antigen.

Thus the invention provides an immunogenic composition comprising: (a) a conjugated capsular saccharide from *S. pneumoniae*, (b) a conjugated capsular saccharide from *N. meningitidis* serogroup C, and (c) inactivated poliovirus antigen. The composition may also include one or more of: a diphtheria toxoid; a tetanus toxoid; a *B. pertussis* antigen; a HBsAg; and/or a conjugated Hib saccharide.

The invention also provides a kit, comprising at least a first immunogenic component and a second immunogenic component, wherein: (a) one of the components comprises a conjugated capsular saccharide from *S. pneumoniae*, (b) one of the components comprises a conjugated capsular saccharide from *N. meningitidis* serogroup C, (c) one of the components comprises an inactivated poliovirus antigen.

Antigens (a), (b) and (c) are all present within the kit, but they are not all part of the same kit component. The following arrangements of antigens are possible, with up to three separate components for antigens (a), (b) and (c):

| Component 1 | (a)       | (a) & (b) | (a) & (c) | (a) |
|-------------|-----------|-----------|-----------|-----|
| Component 2 | (b) & (c) | (c)       | (b)       | (b) |
| Component 3 | —         | —         | —         | (c) |

The kit may also include one or more of: a diphtheria toxoid; a tetanus toxoid; a *B. pertussis* antigen; a HBsAg; and/or a conjugated Hib saccharide. These additional antigens may be included within the same kit component as any of (a), (b) or (c), or may be in separate component(s). Typically, however, a single kit component can include all of: an inactivated poliovirus antigen; a diphtheria toxoid; a tetanus toxoid; a *B. pertussis* antigen; and a HBsAg.

Combinations of the First, Second, Third, Fourth, Fifth, Sixth, Seventh, Eighth and Ninth Aspects The nine aspects of the invention can be exploited separately, or in combinations of 2, 3, 4, 5, 6, 7, 8 or 9 of the aspects. For example, the invention also provides the following kits:

A kit, comprising a first immunogenic component and a second immunogenic component, wherein: (a) the first immunogenic component comprises a conjugated capsular saccharide from *N. meningitidis* serogroup C; and (b) the second immunogenic component comprises an acellular *B. pertussis* antigen and an inactivated poliovirus antigen.

A kit, comprising a first immunogenic component, a second immunogenic component and a third immunogenic component, wherein: (a) the first immunogenic component comprises a conjugated capsular saccharide from *N. meningitidis* serogroup C; (b) the second immunogenic component comprises an acellular *B. pertussis* antigen and/or an inactivated poliovirus antigen; and (c) the third immunogenic component comprises a conjugated capsular saccharide from *S. pneumoniae*.

A kit, comprising a first immunogenic component and a second immunogenic component and, optionally, a third component, wherein: (a) the first immunogenic component comprises a conjugated capsular saccharide from *N. meningitidis* serogroup C, but does not include an aluminium phosphate adjuvant; (b) the second immunogenic component comprises an acellular *B. pertussis* antigen and/or an inactivated poliovirus antigen; and (c) the optional third component comprises a conjugated capsular saccharide from *S. pneumoniae*.

A kit comprising a first immunogenic component and a second immunogenic component, wherein: (a) the first immunogenic component comprises a conjugated capsular saccharide from *N. meningitidis* serogroup C; (b) the second immunogenic component comprises a diphtheria toxoid, a tetanus toxoid, an acellular *B. pertussis* antigen, a hepatitis B virus surface antigen and an inactivated poliovirus antigen, characterised in that the first immunogenic component is lyophilised and/or does not include an aluminium phosphate adjuvant.

A kit, comprising at least a first immunogenic component and a second immunogenic component, wherein: (a) one of the components comprises a capsular saccharide from *S. pneumoniae*, conjugated to a first carrier protein, (b) one of the components comprises a capsular saccharide from *N. meningitidis* serogroup C, conjugated to a second carrier protein, (c) one of the components comprises an acellular pertussis antigen, characterised in that the first carrier protein and the second carrier protein are the same, and that the component containing the *N. meningitidis* serogroup C is lyophilised and/or does not include an aluminium phosphate adjuvant.

etc.

The invention also provides the following immunogenic compositions:

An immunogenic composition comprising a conjugated capsular saccharide from *N. meningitidis* serogroup C, an acellular *B. pertussis* antigen and an inactivated poliovirus antigen.

An immunogenic composition comprising: (a) a conjugated capsular saccharide from *N. meningitidis* serogroup C, (b) an acellular *B. pertussis* antigen and/or an inactivated poliovirus antigen; and (c) a conjugated capsular saccharide from *S. pneumoniae*.

An immunogenic composition comprising: (a) a capsular saccharide from *S. pneumoniae*, conjugated to a first carrier protein, (b) a capsular saccharide from *N. meningitidis* serogroup C, conjugated to a second carrier protein, and (c) an acellular pertussis antigen, an inactivated poliovirus antigen, and a hepatitis B virus surface antigen, wherein the first carrier protein and the second carrier protein are the same.

etc.

Antigens for Use with the Invention

Compositions and kits of the invention comprise a conjugated *N. meningitidis* serogroup C saccharide antigen. Typically, they also include at least one conjugated *S. pneumoniae* saccharide antigen. They may also include further antigens from other pathogens, particularly from bacteria and/or viruses. Preferred further antigens are selected from:

a diphtheria toxoid ('D')
a tetanus toxoid ('T')
a pertussis antigen ('P'), which is typically acellular ('aP')
a hepatitis B virus (HBV) surface antigen ('HBsAg')
a hepatitis A virus (HAV) antigen
a conjugated *Haemophilus influenzae* type b capsular saccharide ('Hib')
inactivated poliovirus vaccine (IPV)
a conjugated *N. meningitidis* serogroup A capsular saccharide ('MenA')
a conjugated *N. meningitidis* serogroup W135 capsular saccharide ('MenW135')
a conjugated *N. meningitidis* serogroup Y capsular saccharide ('MenY')

More than one of these further antigens can be used. The following combinations of antigens are particularly preferred:

Bivalent vaccines: MenC-PnC.
Tetravalent vaccines: D-T-Pa-MenC.
Pentavalent vaccines: D-T-Pa-Hib-MenC; D-T-Pa-IPV-MenC; D-T-Pa-HBsAg-MenC; D-T-Pa-MenC-PnC.
Hexavalent vaccines: D-T-Pa-HBsAg-IPV-MenC; D-T-Pa-HBsAg-MenC-PnC.
Heptavalent vaccines: D-T-Pa-HBsAg-IPV-Hib-MenC; D-T-Pa-HBsAg-Hib-MenC-MenA.
Octavalent vaccines: D-T-Pa-HBsAg-IPV-Hib-MenC-MenA; D-T-Pa-HBsAg-IPV-Hib-MenC-PnC.

These compositions may consist of the antigens listed, or may further include antigens from additional pathogens. Thus they can be used individually, or as components of further vaccines.

Conjugated *N. meningitidis* Saccharides

Conjugated meningococcal antigens comprise capsular saccharide antigens from *Neisseria meningitidis* conjugated to carrier proteins. Conjugated monovalent vaccines against serogroup C have been approved for human use, and include MENJUGATE™ [13], MENINGITEC™ and NEISVAC-C™. Mixtures of conjugates from serogroups A+C are known [14,15] and mixtures of conjugates from serogroups A+C+W135+Y have been reported [16-19] and were approved in 2005 as the MENACTRA™ product.

The invention uses at least a meningococcal saccharide from serogroup C, but may also include saccharide from one or more of serogroups A, W135 and/or Y e.g. A+C, C+W135, C+Y, A+C+W135, A+C+Y, C+W135+Y, A+C+W135+Y. Where more than one serogroup is used then it is preferred to use both of serogroups A and C.

The meningococcal serogroup C capsular saccharide is an α2→9-linked homopolymer of sialic acid (N-acetyl-neuraminic acid), typically with O-acetyl (OAc) groups at C-7 or C-8 residues. The compound is represented as:

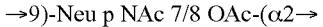
→9)-Neu p NAc 7/8 OAc-(α2→

Some MenC strains (~12% of invasive isolates) produce a polysaccharide that lacks this OAc group. The presence or absence of OAc groups generates unique epitopes, and the specificity of antibody binding to the saccharide may affect its bactericidal activity against O-acetylated (OAc−) and de-O-acetylated (OAc+) strains [20-22]. Licensed MenC conjugate vaccines include both OAc− (NEISVAC-C™) and OAc+ (MENJUGATE™ & MENINGITEC™) saccharides. Serogroup C saccharides used with the invention may be prepared from either OAc+ or OAc− strains. Preferred strains for production of serogroup C conjugates are OAc+ strains, preferably of serotype 16, preferably of serosubtype P1.7a,1. Thus C:16:P1.7a,1 OAc+ strains are preferred. OAc+ strains in serosubtype P1.1 are also useful, such as the C11 strain.

The meningococcal serogroup A capsular saccharide is a homopolymer of (α1→6)-linked N-acetyl-D-mannosamine-1-phosphate, with partial O-acetylation in the C3 and C4 positions. Acetylation at the C-3 position can be 70-95%. Conditions used to purify the saccharide can result in de-O-acetylation (e.g. under basic conditions), but it is preferred to retain OAc at this C-3 position. Thus, preferably at least 50% (e.g. at least 60%, 70%, 80%, 90%, 95% or more) of the mannosamine residues are O-acetylated at the C-3 position.

The serogroup W135 saccharide is a polymer of sialic acid-galactose disaccharide units. Like the serogroup C saccharide, it has variable O-acetylation, but at sialic acid 7 and 9 positions [23]. The structure is written as:

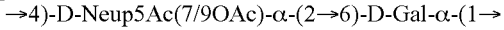
→4)-D-Neup5Ac(7/9OAc)-α-(2→6)-D-Gal-α-(1→

The serogroup Y saccharide is similar to the serogroup W135 saccharide, except that the disaccharide repeating unit includes glucose instead of galactose. Like serogroup W135, it has variable O-acetylation at sialic acid 7 and 9 positions [23]. The serogroup Y structure is written as:

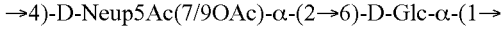
→4)-D-Neup5Ac(7/9OAc)-α-(2→6)-D-Glc-α-(1→

The MENJUGATE™ and MENINGITEC™ products use a CRM197 carrier protein, and this carrier can also be used according to the invention; The NEISVAC-C™ product uses a tetanus toxoid carrier protein, and this carrier can also be used according to the invention, as can diphtheria toxoid. Another useful carrier protein for the meningococcal conjugates is protein D from *Haemophilus influenzae*, which is not present in any existing approved conjugate vaccines.

The saccharide moiety of the conjugate may comprise full-length saccharides as prepared from *meningococci*, and/or it may comprise fragments of full-length saccharides. The saccharides used according to the invention are preferably shorter than the native capsular saccharides seen in bacteria. Thus the saccharides are preferably depolymerised, with depolymerisation occurring after saccharide purification but before conjugation. Depolymerisation reduces the chain length of the saccharides. One depolymerisation method involves the use of hydrogen peroxide [16]. Hydrogen peroxide is added to a saccharide (e.g. to give a final $H_2O_2$ concentration of 1%), and the mixture is then incubated (e.g. at about 55° C.) until a desired chain length reduction has been achieved. Another depolymerisation method involves acid hydrolysis [17]. Other depolymerisation methods are known in the art. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides. Preferred saccharides have the following range of average degrees of polymerisation (Dp): A=10-20; C=12-22; W135=15-25; Y=15-25. In terms of molecular weight, rather than Dp, preferred ranges are, for all serogroups: <100 kDa; 5 kDa-75 kDa; 7 kDa-50 kDa; 8 kDa-35 kDa; 12 kDa-25 kDa; 15 kDa-22 kDa.

Meningococcal conjugates with a saccharide:protein ratio (w/w) of between 1:10 (i.e. excess protein) and 10:1 (i.e. excess saccharide) may be used e.g. ratios between 1:5 and 5:1, between 1:2.5 and 2.5:1, or between 1:1.25 and 1.25:1. A ratio of 1:1 can be used, particularly for serogroup C.

Typically, a composition will include between 1 µg and 20 µg (measured as saccharide) per dose of each serogroup that is present.

Administration of a conjugate preferably results in an increase in serum bactericidal assay (SBA) titre for the relevant serogroup of at least 4-fold, and preferably at least 8-fold. SBA titres can be measured using baby rabbit complement or human complement [24].

Meningococcal conjugates may or may not be adsorbed to an aluminium salt adjuvant.

Meningococcal conjugates may be lyophilised prior to use according to the invention. If lyophilised, the composition may include a stabiliser such as mannitol. It may also include sodium chloride.

Conjugated Pneumococcal Saccharides

Conjugated pneumococcal antigens comprise capsular saccharide antigens from *Streptococcus pneumoniae* conjugated to carrier proteins [e.g. refs. 25 to 27]. It is preferred to include saccharides from more than one serotype of *S. pneumoniae*: mixtures of polysaccharides from 23 different serotype are widely used, as are conjugate vaccines with polysaccharides from between 5 and 11 different serotypes [28]. For example, PREVNAR™ [29] contains antigens from seven serotypes (4, 6B, 9V, 14, 18C, 19F, and 23F) with each saccharide individually conjugated to CRM197 by reductive amination, with 2 µg of each saccharide per 0.5 ml dose (4 µg of serotype 6B).

Compositions of the invention preferably include saccharide antigens for at least serotypes 6B, 14, 19F and 23F. Further serotypes are preferably selected from: 1, 3, 4, 5, 7F, 9V and 18C. 7-valent (as in PREVNAR™), 9-valent (e.g. the 7 serotypes from PREVNAR, plus 1 & 5), 10-valent (e.g. the 7 serotypes from PREVNAR, plus 1, 5 & 7F) and 11-valent (e.g. the 7 serotypes from PREVNAR, plus 1, 3, 5 & 7F) coverage of pneumococcal serotypes is particularly useful.

The saccharide moiety of the conjugate may comprise full-length saccharides as prepared from *pneumococci*, and/or it may comprise fragments of full-length saccharides. The saccharides used according to the invention are preferably shorter than the native capsular saccharides seen in bacteria, as described above for meningococcal conjugates.

Pneumococcal conjugates with a saccharide:protein ratio (w/w) of between 1:10 (i.e. excess protein) and 10:1 (i.e. excess saccharide) may be used e.g. ratios between 1:5 and 5:1, between 1:2.5 and 2.5:1, or between 1:1.25 and 1.25:1.

The PREVNAR™ product use a CRM197 carrier protein, and this carrier can also be used according to the invention. Alternative carriers for use with pneumococcal saccharides include, but are not limited to, a tetanus toxoid carrier, a diphtheria toxoid carrier, and/or a *H. influenzae* protein D carrier. The use of multiple carriers for mixed pneumococcal serotypes may be advantageous [30] e.g. to include both a *H. influenzae* protein D carrier and e.g. a tetanus toxoid carrier and/or a diphtheria toxoid carrier. For example, one or more (preferably all) of serotypes 1, 4, 5, 6B, 7F, 9V, 14 and 23F may be conjugated to a *H. influenzae* protein D carrier, serotype 18C may be conjugated to a tetanus toxoid, and serotype 19F may be conjugated to a diphtheria toxoid carrier.

Typically, a composition will include between 1 µg and 20 µg (measured as saccharide) per dose of each serotype that is present.

Pertussis Antigens

*Bordetella pertussis* causes whooping cough. Pertussis antigens in vaccines are either cellular (whole cell, in the form of inactivated *B. pertussis* cells) or acellular. Preparation of cellular pertussis antigens is well documented [e.g. see chapter 21 of ref. 1] e.g. it may be obtained by heat inactivation of phase I culture of *B. pertussis*. Preferably, however, the invention uses acellular antigens.

Where acellular antigens are used, it is preferred to use one, two or (preferably) three of the following antigens: (1) detoxified pertussis toxin (pertussis toxoid, or 'PT'); (2) filamentous hemagglutinin ('FHA'); (3) pertactin (also known as the '69 kiloDalton outer membrane protein'). These three antigens are preferably prepared by isolation from *B. pertussis* culture grown in modified Stainer-Scholte liquid medium. PT and FHA can be isolated from the fermentation broth (e.g. by adsorption on hydroxyapatite gel), whereas pertactin can be extracted from the cells by heat treatment and flocculation (e.g. using barium chloride). The antigens can be purified in successive chromatographic and/or precipitation steps. PT and FHA can be purified by, for example, hydrophobic chromatography, affinity chromatography and size exclusion chromatography. Pertactin can be purified by, for example, ion exchange chromatography, hydrophobic chromatography and size exclusion chromatography. FHA and pertactin may be treated with formaldehyde prior to use according to the invention. PT is preferably detoxified by treatment with formaldehyde and/or glutaraldehyde. As an alternative to this chemical detoxification procedure the PT may be a mutant PT in which enzymatic activity has been reduced by mutagenesis [31], but detoxification by chemical treatment is preferred.

Acellular pertussis antigens are preferably adsorbed onto one or more aluminium salt adjuvants. As an alternative, they may be added in an unadsorbed state. Where pertactin is added then it is preferably already adsorbed onto an aluminum hydroxide adjuvant. PT and FHA may be adsorbed onto an aluminum hydroxide adjuvant or an aluminum phosphate. Adsorption of all of PT, FHA and pertactin to aluminum hydroxide is most preferred.

Compositions will typically include: 1-50 µg/dose PT; 1-50 µg/dose FHA; and 1-50 µg pertactin. Preferred amounts are about 25 µg/dose PT, about 25 µg/dose FHA and about 8 µg/dose pertactin.

As well as PT, FHA and pertactin, it is possible to include fimbriae (e.g. agglutinogens 2 and 3) in an acellular pertussis vaccine.

Inactivated Poliovirus Vaccine

Poliovirus causes poliomyelitis. Rather than use oral poliovirus vaccine, preferred embodiments of the invention use IPV, as disclosed in more detail in chapter 24 of reference 1.

Polioviruses may be grown in cell culture, and a preferred culture uses a Vero cell line, derived from monkey kidney. Vero cells can conveniently be cultured on microcarriers. After growth, virions may be purified using techniques such as ultrafiltration, diafiltration, and chromatography. Prior to administration to patients, polioviruses must be inactivated, and this can be achieved by treatment with formaldehyde.

Poliomyelitis can be caused by one of three types of poliovirus. The three types are similar and cause identical symptoms, but they are antigenically very different and infection by one type does not protect against infection by others. It is therefore preferred to use three poliovirus antigens in the invention: poliovirus Type 1 (e.g. Mahoney strain), poliovirus Type 2 (e.g. MEF-1 strain), and poliovirus Type 3 (e.g. Saukett strain). The viruses are preferably grown, purified and inactivated individually, and are then combined to give a bulk trivalent mixture for use with the invention.

Quantities of IPV are typically expressed in the 'DU' unit (the "D-antigen unit" [32]). It is preferred to use between 1-100 DU per viral type per dose e.g. about 80 DU of Type 1 poliovirus, about 16 DU of type 2 poliovirus, and about 64 DU of type 3 poliovirus.

Poliovirus antigens are preferably not adsorbed to any aluminium salt adjuvant before being used to make compositions of the invention, but they may become adsorbed onto aluminum adjuvant(s) in the vaccine composition during storage.

Diphtheria Toxoid

*Corynebacterium diphtheriae* causes diphtheria. Diphtheria toxin can be treated (e.g. using formalin or formaldehyde) to remove toxicity while retaining the ability to induce specific anti-toxin antibodies after injection. These diphtheria toxoids are used in diphtheria vaccines, and are disclosed in more detail in chapter 13 of reference 1. Preferred diphtheria toxoids are those prepared by formaldehyde treatment. The diphtheria toxoid can be obtained by growing *C. diphtheriae* in growth medium (e.g. Fenton medium, or Linggoud & Fenton medium), which may be supplemented with bovine extract, followed by formaldehyde treatment, ultrafiltration and precipitation. The toxoided material may then be treated by a process comprising sterile filtration and/or dialysis.

Quantities of diphtheria toxoid can be expressed in international units (IU). For example, the NIBSC supplies the 'Diphtheria Toxoid Adsorbed Third International Standard 1999' [33,34], which contains 160 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture [35]. For example, the NIBSC supplies 'Diphtheria Toxoid, Plain' [36], which contains 300 LF per ampoule, and also supplies 'The 1st International Reference Reagent For Diphtheria Toxoid For Flocculation Test' [37] which contains 900 LF per ampoule.

Compositions typically include between 20 and 80 Lf of diphtheria toxoid, typically about 50 Lf.

By IU measurements, compositions will typically include at least 30 IU/dose.

The diphtheria toxoid is preferably adsorbed onto an aluminium hydroxide adjuvant.

Tetanus Toxoid

*Clostridium tetani* causes tetanus. Tetanus toxin can be treated to give a protective toxoid. The toxoids are used in tetanus vaccines, and are disclosed in more detail in chapter 27 of reference 1. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis.

Quantities of tetanus toxoid can be expressed in international units (IU). For example, the NIBSC supplies the 'Tetanus Toxoid Adsorbed Third International Standard 2000' [38, 39], which contains; 469 IU per ampoule. As an alternative to the IU system, the 'Lf' unit ("flocculating units" or the "limes flocculating dose") is defined as the amount of toxoid which, when mixed with one International Unit of antitoxin, produces an optimally flocculating mixture [35]. For example, the NIBSC supplies 'The 1st International Reference Reagent for Tetanus Toxoid For Flocculation Test' [40] which contains 1000 LF per ampoule.

Compositions will typically include between 5 and 50 Lf of diphtheria toxoid, typically about 20 Lf.

By IU measurements, compositions will typically include at least 40 IU/dose.

The tetanus toxoid may be adsorbed onto an aluminium hydroxide adjuvant, but this is not necessary (e.g. adsorption of between 0-10% of the total tetanus toxoid can be used).

Hepatitis A Virus Antigens

Hepatitis A virus (HAV) is one of the known agents which causes viral hepatitis. HAV vaccines are disclosed in chapter 15 of reference 1. A preferred HAV component is based on inactivated virus, and inactivation can be achieved by formalin treatment. Virus can be grown on human embryonic lung diploid fibroblasts, such as MRC-5 cells. A preferred HAV strain is HM175, although CR326F can also be used. The cells can be grown under conditions that permit viral growth. The cells are lysed, and the resulting suspension can be purified by ultrafiltration and gel permeation chromatography.

The amount of HAV antigen, measured in EU (Elisa Units), is typically at least about 500 EU/ml.

Hepatitis B Virus Surface Antigen

Hepatitis B virus (HBV) is one of the known agents which causes viral hepatitis. The HBV virion consists of an inner core surrounded by an outer protein coat or capsid, and the viral core contains the viral DNA genome. The major component of the capsid is a protein known as HBV surface antigen or, more commonly, 'HBsAg', which is typically a 226-amino acid polypeptide with a molecular weight of ~24 kDa. All existing hepatitis B vaccines contain HBsAg, and when this antigen is administered to a normal vaccinee it stimulates the production of anti-HBsAg antibodies which protect against HBV infection.

For vaccine manufacture, HBsAg has been made in two ways. The first method involves purifying the antigen in particulate form from the plasma of chronic hepatitis B carriers, as large quantities of HBsAg are synthesized in the liver and released into the blood stream during an HBV infection. The second way involves expressing the protein by recombinant DNA methods. HBsAg for use with the method of the invention is preferably recombinantly expressed in yeast cells. Suitable yeasts include, for example, *Saccharomyces* (such as *S. cerevisiae*) or *Hanensula* (such as *H. polymorpha*) hosts.

The HBsAg is preferably non-glycosylated. Unlike native HBsAg (i.e. as in the plasma-purified product), yeast-expressed HBsAg is generally non-glycosylated, and this is the most preferred form of HBsAg for use with the invention, because it is highly immunogenic and can be prepared without the risk of blood product contamination.

The HBsAg will generally be in the form of substantially-spherical particles (average diameter of about 20 nm), including a lipid matrix comprising phospholipids. Yeast-expressed HBsAg particles may include phosphatidylinositol, which is not found in natural HBV virions. The particles may also include a non-toxic amount of LPS in order to stimulate the immune system [41]. Preferred HbsAg is in the form of particles including a lipid matrix comprising phospholipids, phosphatidylinositol and polysorbate 20.

All known HBV subtypes contain the common determinant 'a'. Combined with other determinants and subdeterminants, nine subtypes have been identified: ayw1, ayw2, ayw3, ayw4, ayr, adw2, adw4, adrq− and adrq+. Besides these subtypes, other variants have emerged, such as HBV mutants that have been detected in immunised individuals ("escape mutants"). The most preferred HBV subtype for use with the invention is subtype adw2. A preferred HBsAg has the following amino acid sequence (SEQ ID NO: 1):

MENITSGFLGPLLVLQAGFFLLTRILTIPQSLDSWWTSLNFLGGSPVCLG

QNSQSPTSNHSPTSCPPICPGYRWMCLRRFIIFLFILLLCLIFLLVLLDY

QGMLPVCPLIPGSTTTNTGPCKTCTTPAQGNSMFPSCCCTKPTDGNCTCI

PIPSSWAFAKYLWEWASVRFSWLSLLVPFVQWFVGLSPTVWLSAIWMMWY

WGPSLYSIVSPFIPLLPILFFCLWVYI

This sequence differs from the closest database matches at amino acid 117, having an Asn residue rather than Ser. The invention can use SEQ ID NO: 1, or a sequence differing from SEQ ID NO: 1 by up to 10 (i.e. 1, 2, 3, 4, 5, 6, 7, 8, 9 or 10) single amino acid substitutions.

In addition to the 'S' sequence, a surface antigen may include all or part of a pre-S sequence, such as all or part of a pre-S1 and/or pre-S2 sequence.

HBsAg is preferably expressed: (1) under the control of an upstream promoter from a glyceraldehyde-3-phosphate dehydrogenase gene; and/or (2) with a downstream ARG3 transcription terminator.

Glyceraldehyde-3-phosphate dehydrogenase is a glycolytic enzyme, and its promoter has been found to be particularly suitable for controlling expression of HBsAg in *S. cerevisiae [*42]. A preferred GAPDH promoter comprises the following 1060-mer nucleotide sequence (SEQ ID NO: 2):

AAGCTTACCAGTTCTCACACGGAACACCACTAATGGACACACATTCGAAA

TACTTTGACCCTATTTTCGAGGACCTTGTCACCTTGAGCCCAAGAGAGCC

AAGATTTAAATTTTCCTATGACTTGATGCAAATTCCCAAAGCTAATAACA

TGCAAGACACGTACGGTCAAGAAGACATATTTGACCTCTTAACAGGTTCA

GACGCGACTGCCTCATCAGTAAGACCCGTTGAAAAGAACTTACCTGAAAA

AAACGAATATATACTAGCGTTGAATGTTAGCGTCAACAACAAGAAGTTTA

CTGACGCGGAGGCCAAGGCAAAAAGATTCCTTGATTACGTAAGGGAGTTA

GAATCATTTTGAATAAAAAACACGCTTTTTCAGTTCGAGTTTATCATTAT

CAATACTGCCATTTCAAAGAATACGTAAATAATTAATAGTAGTGATTTTC

CTAACTTTATTTAGTCAAAAAATTAGCCTTTTAATTCTGCTGTAACCCGT

ACATGCCCAAAATAGGGGGCGGGTTACACAGAATATATAACATCGTAGGT

GTCTGGGTGAACAGTTTATTCCTGGCATCCACTAAATATAATGGAGCCCG

-continued

CTTTTTAAGCTGGCATCCAGAAAAAAAAAGAATCCCAGCACCAAAATATT

GTTTTCTTCACCAACCATCAGTTCATAGGTCCATTCTCTTAGCGCAACTA

CAGAGAACAGGGGCACAAACAGGCAAAAAACGGGCACAACCTCAATGGAG

TGATGCAACCTGCCTGGAGTAAATGATGACACAAGGCAATTGACCCACGC

ATGTATCTATCTCATTTTCTTACACCTTCTATTACCTTCTGCTCTCTCTG

ATTTGGAAAAAGCTGAAAAAAAAGGTTGAAACCAGTTCCCTGAAATTATT

CCCCTACTTGACTAATAAGTATATAAAGACGGTAGGTATTGATTGTAATT

CTGTAAATCTATTTCTTAAACTTCTTAAATTCTACTTTTATAGTTAGTCT

TTTTTTTAGTTTTAAAACACCAAGAACTTAGTTTCGAATAAACACACATA

AACAAACAAA

This sequence differs from the sequence in reference 42 as follows: (1) A/C substitution at nucleotide 42; (2) T/A substitution at nucleotide 194; (3) C/A mutation at nucleotide 301; (4) A insertion at nucleotide 471; (5) C/T substitution at residue 569; (6) T/C substitution at residue 597; (7) T insertion at nucleotide 604 (penta-T instead of tetra-T); and (8) replacement of 3' GCTT sequence with a single. A.

The invention can use this 1060-mer promoter sequence, or a sequence differing from this 1060-mer sequence by up to 20 (i.e. 1, 2, 3, 4, 5, 6, 7, 8, 9, 10, 11, 12, 13, 14, 15, 16, 17, 18, 19 or 20) point mutations, each point mutation being the deletion, substitution or insertion of a single nucleotide.

The 1060-mer sequence is preferably immediately downstream of the ATG start codon encoding the N-terminus of the HBsAg (SEQ ID NO: 3):

AAGCTTACCAGTTCTCACACGGAACACCACTAATGGACACACATTCGAAA

TACTTTGACCCTATTTTCGAGGACCTTGTCACCTTGAGCCCAAGAGAGCC

AAGATTTAAATTTTCCTATGACTTGATGCAAATTCCCAAAGCTAATAACA

TGCAAGACACGTACGGTCAAGAAGACATATTTGACCTCTTAACAGGTTCA

GACGCGACTGCCTCATCAGTAAGACCCGTTGAAAAGAACTTACCTGAAAA

AAACGAATATATACTAGCGTTGAATGTTAGCGTCAACAACAAGAAGTTTA

CTGACGCGGAGGCCAAGGCAAAAAGATTCCTTGATTACGTAAGGGAGTTA

GAATCATTTTGAATAAAAAACACGCTTTTTCAGTTCGAGTTTATCATTAT

CAATACTGCCATTTCAAAGAATACGTAAATAATTAATAGTAGTGATTTTC

CTAACTTTATTTAGTCAAAAAATTAGCCTTTTAATTCTGCTGTAACCCGT

ACATGCCCAAAATAGGGGGCGGGTTACACAGAATATATAACATCGTAGGT

GTCTGGGTGAACAGTTTATTCCTGGCATCCACTAAATATAATGGAGCCCG

CTTTTTAAGCTGGCATCCAGAAAAAAAAAGAATCCCAGCACCAAAATATT

GTTTTCTTCACCAACCATCAGTTCATAGGTCCATTCTCTTAGCGCAACTA

CAGAGAACAGGGGCACAAACAGGCAAAAAACGGGCACAACCTCAATGGAG

TGATGCAACCTGCCTGGAGTAAATGATGACACAAGGCAATTGACCCACGC

ATGTATCTATCTCATTTTCTTACACCTTCTATTACCTTCTGCTCTCTCTG

ATTTGGAAAAAGCTGAAAAAAAAGGTTGAAACCAGTTCCCTGAAATTATT

CCCCTACTTGACTAATAAGTATATAAAGACGGTAGGTATTGATTGTAATT

CTGTAAATCTATTTCTTAAACTTCTTAAATTCTACTTTTATAGTTAGTCT

```
-continued
TTTTTTTAGTTTTAAAACACCAAGAACTTAGTTTCGAATAAACACACATA

AACAAACAAAATG . . .
```

The ARG3 gene in yeast encodes the ornithine carbamoyltransferase enzyme [43] and its transcription termination sequence has been used in several yeast recombinant expression systems [44, 45, 46]. It is advantageous for the control of HBsAg expression in yeast, particularly in combination with a GAPDH promoter.

The gene encoding HBsAg will typically be an insert in a plasmid. A preferred plasmid includes a GAPDH promoter, followed by a sequence encoding HBsAg, followed by an ARG3 terminator. Preferred plasmids may also include one, two or all three of: (1) a LEU2 selection marker; (2) a 2μ plasmid sequence; and/or (3) an origin of replication functional in Escherichia coli [46]. Thus preferred plasmids can act as shuttle vectors between yeast and E. coli.

A plasmid with between 14500 and 15000 bp is preferred e.g. between 14600 and 14700 bp.

Where a LEU2 selection marker is used then the host cell should be LEU2$^{-ve}$ (i.e. a leucine auxotroph). The host cell may be a leu2-3 leu2-112 mutant. Further characteristics of preferred yeast hosts are his3 and/or can1-11. A most preferred yeast host is leu2-3 leu2-112 his3 can1-11, such as the DC5 strain.

A preferred method for HBsAg purification involves, after cell disruption: ultrafiltration; size exclusion chromatography; anion exchange chromatography; ultracentrifugation; desalting; and sterile filtration. Lysates may be precipitated after cell disruption (e.g. using a polyethylene glycol), leaving HBsAg in solution, ready for ultrafiltration.

After purification HBsAg may be subjected to dialysis (e.g. with cysteine), which can be used to remove any mercurial preservatives such as thimerosal that may have been used during HBsAg preparation [47].

Quantities of HBsAg are typically expressed in micrograms, and a typical amount of HBsAg per vaccine dose is between 5 and 5 μg e.g. 10 μg/dose.

Although HBsAg may be adsorbed to an aluminium hydroxide adjuvant in the final vaccine (as in the well-known ENGERIX-B™ product), or may remain unadsorbed, it will generally be adsorbed to an aluminium phosphate adjuvant [48].

Conjugated *Haemophilus influenzae* Type B Antigens

*Haemophilus influenzae* type b ('Hib') causes bacterial meningitis. Hib vaccines are typically based on the capsular saccharide antigen [e.g. chapter 14 of ref. 1], the preparation of which is well documented [e.g. references 49 to 58].

The Hib saccharide can be conjugated to a carrier protein in order to enhance its immunogenicity, especially in children. Typical carrier proteins are tetanus toxoid, diphtheria toxoid, the CRM197 derivative of diphtheria toxoid, *H. influenzae* protein D, and an outer membrane protein complex from serogroup B. *meningococcus*. The carrier protein in the Hib conjugate is preferably different from the carrier protein(s) in the meningococcal conjugate(s), but the same carrier can be used in some embodiments.

Tetanus toxoid is the preferred carrier, as used in the product commonly referred to as 'PRP-T'. PRP-T can be made by activating a Hib capsular polysaccharide using cyanogen bromide, coupling the activated saccharide to an adipic acid linker (such as (1-ethyl-3-(3-dimethylaminopropyl) carbodiimide), typically the hydrochloride salt), and then reacting the linker-saccharide entity with a tetanus toxoid carrier protein.

The saccharide moiety of the conjugate may comprise full-length polyribosylribitol phosphate (PRP) as prepared from Hib bacteria, and/or fragments of full-length PRP.

Hib conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. In preferred vaccines, however, the weight ratio of saccharide to carrier protein is between 1:2 and 1:4, preferably between 1:2.5 and 1:3.5. In vaccines where tetanus toxoid is present both as an antigen and as a carrier protein then the weight ratio of saccharide to carrier protein in the conjugate may be between 1:0.3 and 1:2 [59].

Amounts of Hib conjugates are generally given in terms of mass of saccharide (i.e. the dose of the conjugate (carrier+saccharide) as a whole is higher than the stated dose) in order to avoid variation due to choice of carrier. A typical amount of Hib saccharide per dose is between 1-30 μg, preferably about 10 μg.

Administration of the Hib conjugate preferably results in an anti-PRP antibody concentration of ≧0.15 μg/ml, and more preferably ≧1 μg/ml, and these are the standard response thresholds.

Hib conjugates may be lyophilised prior to their use according to the invention. Further components may also be added prior to freeze-drying e.g. as stabilizers. Preferred stabilizers for inclusion are lactose, sucrose and mannitol, as well as mixtures thereof e.g. lactose/sucrose mixtures, sucrose/mannitol mixtures, etc. The final vaccine may thus contain lactose and/or sucrose. Using a sucrose/mannitol mixture can speed up the drying process.

Hib conjugates may or may not be adsorbed to an aluminium salt adjuvant. It is preferred not to adsorb them to an aluminium hydroxide adjuvant.

Characteristics of Compositions of the Invention

In addition to the antigenic components described above, compositions of the invention will generally include a non-antigenic component. The non-antigenic component can include carriers, adjuvants, excipients, buffers, etc., as described in more detail below. These non-antigenic components may have various sources. For example, they may be present in one of the antigen or adjuvant materials that is used during manufacture or may be added separately from those components.

Preferred compositions of the invention include one or more pharmaceutical carrier(s) and/or excipient(s).

To control tonicity, it is preferred to include a physiological salt, such as a sodium salt. Sodium chloride (NaCl) is preferred, which may be present at between 1 and 20 mg/ml.

Compositions will generally have an osmolality of between 200 mOsm/kg and 400 mOsm/kg, preferably between 240-360 mOsm/kg, and will more preferably fall within the range of 290-320 mOsm/kg. Osmolality has previously been reported not to have an impact on pain caused by vaccination [60], but keeping osmolality in this range is nevertheless preferred.

Compositions of the invention may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition of the invention will generally be between 5.0 and 7.5, and more typically between 5.0 and 6.0 for optimum stability, or between 6.0 and 7.0.

Compositions of the invention are preferably sterile.

Compositions of the invention are preferably non-pyrogenic e.g. containing <1 EU (endotoxin unit, a standard measure) per dose, and preferably <0.1 EU per dose.

Compositions of the invention are preferably gluten free.

Where antigens are adsorbed, a composition may be a suspension with a cloudy appearance. This appearance means that microbial contamination is not readily visible, and so the vaccine preferably contains a preservative. This is particularly important when the vaccine is packaged in multidose containers. Preferred preservatives for inclusion are 2-phenoxyethanol and thimerosal. It is recommended, however, not to use mercurial preservatives (e.g. thimerosal) where possible. It is preferred that compositions of the invention contain less than about 25 ng/ml mercury.

The concentration of any aluminium salts in a composition of the invention, expressed in terms of $Al^{3+}$, is preferably less than 5 mg/ml e.g. $\leq 4$ mg/ml, $\leq 3$ mg/ml, $\leq 2$ mg/ml, $\leq 1$ mg/ml, etc.

Compositions of the invention are preferably administered to patients in 0.5 ml doses. References to 0.5 ml doses will be understood to include normal variance e.g. 0.5 ml±0.05 ml.

The invention can provide bulk material which is suitable for packaging into individual doses, which can then be distributed for administration to patients. Concentrations mentioned above are typically concentrations in final packaged dose, and so concentrations in bulk vaccine may be higher (e.g. to be reduced to final concentrations by dilution).

Residual material from individual antigenic components may also be present in trace amounts in the final vaccine produced by the process of the invention. For example, if formaldehyde is used to prepare the toxoids of diphtheria, tetanus and pertussis then the final vaccine product may retain trace amounts of formaldehyde (e.g. less than 10 μg/ml, preferably <5 μg/ml). Media or stabilizers may have been used during poliovirus preparation (e.g. Medium 199), and these may carry through to the final vaccine. Similarly, free amino acids (e.g. alanine, arginine, aspartate, cysteine and/or cystine, glutamate, glutamine, glycine, histidine, proline and/or hydroxyproline, isoleucine, leucine, lysine, methionine, phenylalanine, serine, threonine, tryptophan, tyrosine and/or valine), vitamins (e.g. choline, ascorbate, etc.), disodium phosphate, monopotassium phosphate, calcium, glucose, adenine sulfate, phenol red, sodium acetate, potassium chloride, etc. may be retained in the final vaccine at $\leq 100$ μg/ml, preferably <10 μg/ml, each. Other components from antigen preparations, such as neomycin (e.g. neomycin sulfate, particularly from the IPV component), polymyxin B (e.g. polymyxin B sulfate, particularly from the IPV component), etc. may also be present e.g. at sub-nanogram amounts per dose.

A further possible component of the final vaccine which originates in the antigen preparations arises from less-than-total purification of antigens. Small amounts of *B. pertussis*, *C. diphtheriae*, *C. tetani* and/or *S. cerevisiae* proteins and/or genomic DNA may therefore be present.

Where an IPV component is used, it will generally have been grown on Vero cells. The final vaccine preferably contains less than 50 pg/ml of Vero cell DNA e.g. less than 50 pg/ml of Vero cell DNA that is $\geq 50$ base pairs long.

Adjuvants

Preferred immunogenic compositions of the invention include an adjuvant, and this adjuvant preferably comprises one or more aluminium salts, and particularly an aluminium phosphate adjuvant and/or an aluminium hydroxide adjuvant. Antigenic components used to prepare compositions of the invention preferably include aluminium adjuvants before being used i.e. they are 'pre-mixed' or 'pre-adsorbed' to the adjuvant(s).

Aluminium adjuvants currently in use are typically referred to either as "aluminium hydroxide" or as "aluminium phosphate" adjuvants. These are names of convenience, however, as neither is a precise description of the actual chemical compound which is present (e.g. see chapter 9 of reference 61). The invention can use any of the "hydroxide" or "phosphate" salts that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ (chapter 9 of ref. 61).

The adjuvants known as "aluminium phosphate" are typically aluminium hydroxyphosphates, often also containing a small amount of sulfate. They may be obtained by precipitation, and the reaction conditions and concentrations during precipitation can influence the degree of substitution of phosphate for hydroxyl in the salt. Hydroxyphosphates generally have a $PO_4$/Al molar ratio between 0.3 and 0.99. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls (chapter 9 of ref. 61).

The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate. Typical diameters of the particles are in the range 0.5-20 μm (e.g. about 5-10 μm) after any antigen adsorption.

The PZC of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

An aluminium phosphate solution used to prepare a composition of the invention may contain a buffer (e.g. a phosphate or a histidine or a Tris buffer), but this is not always necessary. The aluminium phosphate solution is preferably sterile and pyrogen-free. The aluminium phosphate solution may include free aqueous phosphate ions e.g. present at a concentration between 1.0 and 20 mM, preferably between 5 and 15 mM, and more preferably about 10 mM. The aluminium phosphate solution may also comprise sodium chloride. The concentration of sodium chloride is preferably in the range of 0.1 to 100 mg/ml (e.g. 0.5-50 mg/ml, 1-20 mg/ml, 2-10 mg/ml) and is more preferably about 3±1 mg/ml. The presence of NaCl facilitates the correct measurement of pH prior to adsorption of antigens.

Methods of Treatment and Administration of the Vaccine

The invention involves the co-administration of antigens from different pathogens. These antigens may be co-administered in the form of a combination vaccine (i.e. a single aqueous composition containing multiple antigens, such that its administration simultaneously immunises a subject against multiple pathogens). Alternatively, they may be co-administered separately to a patient (e.g. at different sites), but at substantially the same time as each other e.g. during the same consultation with a physician or other health care provider. Thus the different antigens may be for simultaneous separate or sequential use, or they may be for mixing prior to use. Administration of different conjugate vaccines simultaneously but at different sites may avoid potential suppression effects seen where the conjugates share a carrier protein.

Compositions of the invention are suitable for administration to human patients, and the invention provides a method of raising an immune response in a patient, comprising the step of administering a composition of the invention to the patient.

The invention also provides a composition of the invention for use in medicine.

The invention also provides the use of (a) a conjugated capsular saccharide from *N. meningitidis* serogroup C and (b) an acellular *B. pertussis* antigen, in the manufacture of a medicament for immunising a patient.

The invention also provides the use of (a) a conjugated capsular saccharide from *N. meningitidis* serogroup C and (b) an inactivated poliovirus antigen, in the manufacture of a medicament for immunising a patient.

The invention also provides the use of (a) a conjugated capsular saccharide from *N. meningitidis* serogroup C, (b) a conjugated capsular saccharide from *S. pneumoniae*, (c) a hepatitis B virus surface antigen, in the manufacture of a medicament for immunising a patient.

The invention also provides the use of (a) a conjugated capsular saccharide from *N. meningitidis* serogroup C, (b) a conjugated capsular saccharide from *S. pneumoniae*, (c) an inactivated poliovirus antigen, in the manufacture of a medicament for immunising a patient.

The invention also provides the use of (a) a conjugated capsular saccharide from *N. meningitidis* serogroup C, (b) a conjugated capsular saccharide from *S. pneumoniae*, (c) an inactivated poliovirus antigen, and (d) an acellular *B. pertussis* antigen, in the manufacture of a medicament for immunising a patient.

The invention also provides the use of (a) a capsular saccharide from *N. meningitidis* serogroup C, conjugated to a first carrier protein, (b) a capsular saccharide from *S. pneumoniae* conjugated to a second carrier protein, in the manufacture of a medicament for immunising a patient, characterised in that the first carrier protein and the second carrier protein are the same.

Immunogenic compositions of the invention are preferably vaccines, for use in the reduction or prevention of diseases such as: bacterial meningitis, including meningococcal meningitis, pneumococcal meningitis and Hib meningitis; viral hepatitis, including HBV and HAV infections; diphtheria; tetanus, or lockjaw; whooping cough, or pertussis; and/or poliomyelitis.

Preferred patients for receiving the compositions of the invention are less than 2 years old, preferably aged between 0-12 months. One particular group of patients is aged between 1 and 3 months, and has not previously received a meningococcal conjugate vaccine. Another group of patients is aged between 3 and 5 months and has previously received a diphtheria toxoid immunisation.

In order to have full efficacy, a typical primary immunization schedule for a child may involve administering more than one dose. For example, doses may be at: 0, 2 and 4 months (time 0 being the first dose); 0, 1 and 2 months; 0 and 2 months; 0, 2 and 8 months; etc. The first dose (time 0) may be administered at about 2 months of age, or sometimes (e.g. in a 0-2-8 month schedule) at around 3 months of age.

Compositions can also be used as booster doses e.g. for children, in the second year of life.

Compositions of the invention can be administered by intramuscular injection e.g. into the arm, leg or buttock. Where separate administration is used then, particularly where there are two separate compositions to be co-administered, it is typical to inject compositions into opposite limbs e.g. to inject into both the left and right arms.

Where compositions of the invention include an aluminium-based adjuvant, settling of components may occur during storage. The composition should therefore be shaken prior to administration to a patient. The shaken composition will generally be a turbid white suspension.

Packaging Compositions of the Invention

Compositions of the invention can be placed into containers for use. Suitable containers include vials and disposable syringes (preferably sterile ones).

Where a composition of the invention is packaged into vials, these are preferably made of a glass or plastic material. The vial is preferably sterilized before the composition is added to it. To avoid problems with latex-sensitive patients, vials are preferably sealed with a latex-free stopper. The vial may include a single dose of vaccine, or it may include more than one dose (a 'multidose' vial) e.g. 10 doses. When using a multidose vial, each dose should be withdrawn with a sterile needle and syringe under strict aseptic conditions, taking care to avoid contaminating the vial contents. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where the composition is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine.

The syringe will generally have a tip cap to seal the tip prior to attachment of a needle, and the tip cap is preferably made of butyl rubber. If the syringe and needle are packaged separately then the needle is preferably fitted with a butyl rubber shield. Grey butyl rubber is preferred. Preferred syringes are those marketed under the trade name "Tip-Lok"™.

Where a glass container (e.g. a syringe or a vial) is used, then it is preferred to use a container made from a borosilicate glass rather than from a soda lime glass.

Various kits are provided by the invention. The kits can comprise separate immunogenic compositions, and these compositions can either be mixed with each other extemporaneously at the time of use, to give a combination vaccine, or they can be administered separately (e.g. at different sites), but at substantially the same time. Thus the compositions in the kit may be for simultaneous separate or sequential use, or they may be for mixing. Where the compositions are to be mixed, it is preferred that at least one of them is initially in aqueous form and one is initially in lyophilised form, such at the lyophilised composition is re-activated by the aqueous composition at the time of use. Where a lyophilised component is present, it will typically comprise one or more conjugated saccharide antigens.

Typical compositions for separate inclusion in kits of the invention include: a composition comprising a MenC conjugate antigen; a composition comprising a pneumococcal conjugate antigen; a composition including acellular *B. pertussis* antigen(s) and/or an inactivated poliovirus antigen; and a composition including a Hib conjugate.

A composition including acellular *B. pertussis* antigen(s) will typically also include a diphtheria toxoid and a tetanus toxoid. It may also include one or more of: a HBsAg and/or IPV. Thus one composition of the kit could be a pentavalent D-T-Pa-HBsAg-IPV composition, or a full-liquid D-T-Pa-HBsAg-IPV-Hib component.

Each composition in the kit can be stored separately e.g. each in a separate vial or syringe. It is also possible to supply one composition in a syringe and the others in vials. Where components are to be mixed extemporaneously at the time of use, an alternative arrangement to having separate containers is to use a multi-chamber container. A multi-chamber syringe allows the individual compositions to be kept separately during storage, but to be mixed as the syringe plunger is activated.

When not supplied in kit form, compositions of the invention may be in full-liquid form.

Immunisation Schedules

As mentioned above, a typical primary immunization schedule for a child involves administering more than one dose. For example, doses may be at: 0, 2 and 4 months (time 0 being the first dose); 0, 1 and 2 months; 0 and 2 months; etc. The first dose (time 0) is usually at about 2 months of age.

A 2-dose schedule (e.g. two months apart) has been found to be non-inferior to a more expensive 3-dose schedule (e.g. 1 month apart). Normal non-meningococcal vaccines can be given between the 2 doses of the 2-dose schedule.

Thus the invention provides a method of treating an patient who has previously received (i) a single dose of a capsular saccharide from *N. meningitidis* serogroup C and (ii) more than one dose of one or more of an acellular *B. pertussis* antigen, hepatitis B virus surface antigen and/or inactivated poliovirus, comprising administering to the patient a further dose of a capsular saccharide from *N. meningitidis* serogroup C. The further MenC dose may optionally be co-administered with other antigens, as described above.

The invention also provides a method for raising an immune response in a patient, comprising the steps of: (i) co-administering to the patient a capsular saccharide from *N. meningitidis* serogroup C and one or more of an acellular *B. pertussis* antigen, hepatitis B virus surface antigen and/or inactivated poliovirus; then (ii) administering to the patient one or more of an acellular *B. pertussis* antigen, hepatitis B virus surface antigen and/or inactivated poliovirus, without co-administering a capsular saccharide from *N. meningitidis* serogroup C; and (iii) co-administering to the patient a capsular saccharide from *N. meningitidis* serogroup C and one or more of an acellular *B. pertussis* antigen, hepatitis B virus surface antigen and/or inactivated poliovirus. Steps (i), (ii) and (iii) are preferably performed in sequence at intervals of at least one month. They may be performed at about 2 months of age, at about 3 months, and at about 4 months. The method can conveniently be implemented by administering: (i) a first vaccine and a second vaccine; (ii) the second vaccine but not the first vaccine; and (iii) the first vaccine and the second vaccine.

In an alternative schedule, steps (ii) and (iii) may be reversed i.e. a patient received the serogroup C vaccine in the first and second visit, but not in the third visit.

The invention also provides the use of a conjugated capsular saccharide from *N. meningitidis* serogroup C in the manufacture of a medicament for immunising a patient, wherein the patient has previously received (i) n doses of a capsular saccharide from *N. meningitidis* serogroup C and (ii) more than n doses of one or more of an acellular *B. pertussis* antigen, hepatitis B virus surface antigen and/or inactivated poliovirus. The value of n is preferably 1.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where an antigen is described as being "adsorbed" to an adjuvant, it is preferred that at least 50% (by weight) of that antigen is adsorbed e.g. 50%, 60%, 70%, 80%, 90%, 95%, 98% or more. It is preferred that diphtheria toxoid and tetanus toxoid are both totally adsorbed i.e. none is detectable in supernatant. Total adsorption of HBsAg is also preferred.

Amounts of conjugates are generally given in terms of mass of saccharide (i.e. the dose of the conjugate (carrier+saccharide) as a whole is higher than the stated dose) in order to avoid variation due to choice of carrier.

Typical carrier proteins for use in conjugates are bacterial toxins, such as diphtheria toxin [e.g. see chapter 13 of ref. 1; refs. 62-65] (or its CRM197 mutant [66-69]) and tetanus toxin, usually in toxoid form (e.g. obtained by treatment with an inactivating chemical, such as formalin or formaldehyde). Other suitable carrier proteins include, but are not limited to, *N. meningitidis* outer membrane protein [70], synthetic peptides [71,72], heat shock proteins [73,74], pertussis proteins [75, 76], cytokines [77], lymphokines [77], hormones [77], growth factors [77], artificial proteins comprising multiple human $CD4^+$ T cell epitopes from various pathogen-derived antigens [78] such as N19 [79], protein D from *H. influenzae* [80-82], pneumolysin [83], pneumococcal surface protein PspA [84], iron-uptake proteins [85], toxin A or B from *C. difficile* [86], etc.

Where animal (and particularly bovine) materials are used in the culture of cells, they should be obtained from sources that are free from transmissible spongiform encaphalopathies (TSEs), and in particular free from bovine spongiform encephalopathy (BSE).

MODES FOR CARRYING OUT THE INVENTION

It will be understood that the invention will be described by way of example only, and that modifications may be made whilst remaining within the scope and spirit of the invention.

Three Doses at 2, 4 & 6 Months

A study was designed to assess safety and immunogenicity of the MENJUGATE™ vaccine (conjugated meningococcal serogroup C capsular saccharide) when given together with the PREVNAR™ vaccine (conjugated 7-valent pneumococcal capsular saccharide) and/or the INFANRIX-HEXA™ product (D-T-Pa-HBsAg-IPV-Hib).

992 infants, aged 2 months at enrolment, were assigned to one of three vaccination groups, receiving: (1) PREVNAR™ plus INFANRIX-HEXA™; (2) MENJUGATE™ plus INFANRIX-HEXA™; or (3) MENJUGATE™ plus PREVNAR™ plus INFANRIX-HEXA™. The vaccines were administered concomitantly, but at separate injection sites. The study was conducted, with the vaccines being administered at ages 2, 4 and 6 months.

Local erytherma, induration and swelling were slightly lower in group 3 than in group 2 (typically around 5% fewer reactions); tenderness was the same in both groups. Systemic reactions were similar in all groups, but were typically lowest in group 2, although diarrhea was lowest in group 3. In all cases, however, the vaccines were well tolerated and were safe.

For assessing immunogenicity, bactericidal titers (BCA) against MenC were measured in two blood samples from each subject: the first was taken at the time of the first vaccine dose; the second was taken 4-6 weeks after the third dose. The BCA assay used human complement.

The immunological results of the study were uncertain, because Buttery et al. [11] had previously reported that meningococcal serogroup C conjugates were immunologically incompatible with pneumococcal multivalent conjugates. In contrast, however, the study of the present invention showed that 100% of subjects in groups (2) and (3) achieved a protective bactericidal titer (i.e. a rise BCA titers of ≧1:8 in the two blood samples) against *N. meningitidis* serogroup C. Moreover, GMTs between both groups were nearly identical, showing that none of the various non-MenC vaccine components interferes with the immunogenicity of the MenC conjugate.

BCA results were as follows:

| Vaccine group | 2 | 3 | Difference/Ratio |
|---|---|---|---|
| % with ≧1:8 rise in BCA GMTs | 100% (98-100%) | 100% (99-100%) | 0% (−1%-2%) |
| BCA GMT in second sample | 572 (473-690) | 565 (465-686) | 0.99 (0.75-1.3) |

Immunogenicity of the INFANRIX HEXA™ components was not impaired. Antibody titers in the second blood sample against the D, T, P, Hib and HBsAg were measured by ELISA. Antibody titers against poliovirus were measured by the standard neutralisation test. Results were as follows:

| Antigen | Criterion | Group 3 | Group 2 | Difference |
|---|---|---|---|---|
| Diphtheria | ≧0.1 IU/mL | 100% | 100% | 0% |
| Tetanus | ≧0.1 IU/mL | 100% | 100% | 0% |
| Pertussis | ≧4-fold increase | 87% | 89% | −2% |
| Hib | ≧0.15 μg/mL | 96 | 99% | −3% |
| HBsAg | ≧10 mIU/mL | 99% | 99% | 0% |
| Poliovirus type 1 | ≧1:8 | 99% | 100% | 0% |
| Poliovirus type 2 | ≧1:8 | 100% | 100% | 0% |
| Poliovirus type 3 | ≧1:8 | 99% | 100% | 0% |

| Antigen | Criterion | Group 1 | Group 2 | Difference |
|---|---|---|---|---|
| Diphtheria | ≧0.1 IU/mL | 100% | 100% | 0% |
| Tetanus | ≧0.1 IU/mL | 100% | 100% | 0% |
| Pertussis | ≧4-fold increase | 92% | 89% | −3% |
| Hib | ≧0.15 μg/mL | 98% | 99% | 0% |
| HBsAg | ≧10 mIU/mL | 98% | 99% | 2% |
| Poliovirus type 1 | ≧1:8 | 99% | 100% | 1% |
| Poliovirus type 2 | ≧1:8 | 100% | 100% | 0% |
| Poliovirus type 3 | ≧1:8 | 99% | 100% | 1% |

Immunogenicity of the PREVNAR™ components was not significantly impaired. The percentages of patients with ELISA titers≧0.15 μg/mL in the second blood sample were as follows:

| Serotype | Group 3 | Group 1 | Difference |
|---|---|---|---|
| 4 | 95% | 96% | 0% |
| 6B | 91% | 92% | −1% |
| 14 | 94% | 96% | −2% |
| 9V | 95% | 97% | −2% |
| 18C | 96% | 94% | −3% |
| 19F | 94% | 97% | −3% |
| 23F | 91% | 95% | −3% |

Thus the immune response against the MenC saccharide was non-inferior in groups (2) and (3) compared to group (1). The immune response against the hexavalent antigens was similar in the three groups. Thus the immune response against the pneumococcal saccharide was non-inferior in group (3) compared to group (1). These results are consistent with reference 3.

Comparison of 2-Dose and 3-Dose Schedules

INFANRIX-HEXA™ can be administered according to a 3-dose primary schedule at 2, 3 & 4 months of age. Because conjugate vaccines may be inhibited by co-administration with acellular pertussis antigens, a study was designed to assess safety and immunogenicity of the MENJUGATE™ vaccine when given together with the INFANRIX-HEXA™ product with this 3-dose schedule. The meningococcal conjugate was either co-administered with all three hexavalent doses (i.e. at 2, 3 & 4 months of age) or was administered only with the first and third (i.e. at 2 and 4 months). Memory responses against the meningococcal conjugate were assessed by administering an unconjugated mixture of serogroup A and C saccharides at age 12 months, at the same time as a further dose of INFANRIX-HEXA™, with blood being drawn 7 or 28 days later.

241 infants, aged 7-11 weeks at enrolment, were assigned to one of four vaccination groups, receiving: (1) MENJUGATE™ plus INFANRIX-HEXA™ according to the 3-dose schedule, followed by unconjugated A/C and INFANRIX-HEXA™ at 12 months, with blood drawn 1 week later; (2) same as group (1) but with blood drawn 28 days after the unconjugated A/C; (3) MENJUGATE™ plus INFANRIX-HEXA™ according to the 2-dose schedule, with INFANRIX-HEXA™ also being administered at 3 months of age, followed by unconjugated A/C and INFANRIX-HEXA™ at 12 months, with blood drawn 1 week later; (4) same as group (3) but with blood drawn 28 days after the unconjugated A/C. Where more than one dose was administered at the same time, they were administered concomitantly but at separate injection sites.

No clinically relevant difference in local reactogenicity between treatment groups and vaccines was observed. After the MenPS A/C vaccination and the fourth injection of hexavalent vaccine at 12 months, higher proportions of subjects in each group experienced local reactions compared to after the first, second and third injection with either hexavalent vaccine or Menjugate™. Most local reactions occurred within two days of injection and were rated as mild or moderate. No subject reported a severe local reaction to the meningococcal conjugate.

The incidence of solicited systemic reactions, when summed for all injections, was similar between the four treatment groups. At visit 2, which allowed comparing systemic reactions after co-administration of Menjugate™ with hexavalent vaccine (groups 1 and 2) to reactions after hexavalent vaccine alone (groups 3 and 4), no clinically relevant difference was observed. Most systemic reactions occurred between 6 hours and 2 days after injection. No subject experienced rectal temperature≧40.5° C.

One month after primary immunization with Menjugate™, the percentage of vaccinees displaying protective SBA titers (titer≧8) were 98% and 100% for the 2-dose and 3-dose immunization schedules, respectively. Protective SBA titers persisted in 89% (2-dose group), versus 95% (3-dose group) at 8 months post-vaccination. Both immunization schedules induced a more than 100-fold increase in SBA geometric mean titers measured one month after 2 or 3 immunizations.

Upon a single challenge dose of MenPS A/C, subjects primed with either immunization schedule of Menjugate™, showed a 15-fold or greater increase of SBA GMTs compared to pre-challenge. This compares to a 1.09-fold increase observed when a single dose of MenPS A/C was administered in unprimed 12 month-old infants in a historical control group from a previous study. SBA determined 28 days following challenge with MenPS A/C GMTs (groups 2 and 4) tended to be higher compared to those determined at day 7 (groups 1 and 3).

Thus reactogenicity and other safety profiles were similar among all four vaccination groups.

The baseline GMCs of antibodies against Hepatitis B surface antigen were similar in subjects in the 2-dose and 3-dose schedule groups (8.61 IU/l and 5.93 IU/l). At one month after the primary immunizations, these had increased 52-fold and 96-fold, respectively, and protective antibody concentrations≧10 IU/l were present in 99% of subjects of either group.

Thus two injections of meningococcal conjugate, administered at 2 and 4 months of age, primed the immune system for immunological memory in healthy infants. 98% of subjects in the 2-dose groups and 100% of subjects in the 3-dose group achieved a hBCA titre of ≧1:8. The immune response induced by the 2-dose schedule can be considered non-inferior to that induced by the 3-dose schedule. 99% of all subjects developed titers≧10 IU/I in response to the hepatitis B component of the hexavalent vaccination, thus demonstrating non-interference with either the 2-dose or the 3-dose meningococcal schedule.

In conclusion, a 2-dose schedule of meningococcal conjugate, two months apart in infants below 1 year of age, was immunogenic and induced immunological memory when given together with the hexavalent vaccine. The 2-dose immunisation schedule for MenC is not inferior to the 3-dose schedule. There is no evidence for a reduced immunogenicity of co-administered D, T, aP, IPV, HBV or Hib antigens.

A booster dose of meningococcal conjugate may be given to these patients in the second year of life.

7-Valent D-T-aP-HBV-IPV-Hib-MenC Immunisation of Infants

In support of the results described above, reference 87 reports a study of the concurrent use of meningococcal C conjugate vaccine (NEISVAC-C™, with a tetanus toxoid carrier) with DTaP-based combinations, according to two vaccination schedules, one of which included hepatitis B vaccination at birth. Healthy infants were randomized to receive either (i) D-T-aP-HBV-IPV/Hib (INFANRIX HEXA™) at 2, 4, and 6 months or (ii) HBV at birth followed by INFANRIX HEXA™ at 2 and 6 months but D-T-aP-IPV/Hib at 4 months. In both groups, two doses of MenC-TT conjugate were co-administered at 2 and 4 months, and compared with 3 doses of MenC-CRM197 conjugate (MENINGITEC™) co-administered at 2, 4, and 6 months with INFANRIX HEXA™.

All NEISVAC-C™ recipients had seroprotective concentrations of anti-PRP antibodies 1 month after the third vaccine dose and all had SBA-MenC titers≧1:8 after the second dose of NEISVAC-C™. These responses were noninferior to those seen after 3 doses of DTaP-HBV-IPV/Hib and MENINGITEC™. Anti-PRP antibody GMCs were significantly higher in NEISVAC-CT vaccines than in MENINGITEC™ vaccinees. Immune responses to all other co-administered antigens were unimpaired, with seroprotection/seropositivity rates≧98.1% in NEISVAC-C™ vaccinees.

All schedules were well tolerated, with no differences in reactogenicity between study groups.

Thus co-administration of D-T-aP-HBV-IPV/Hib or D-T-aP-IPV/Hib with two doses of a MenC conjugate with a tetanus toxoid carrier was concluded to be safe, well tolerated, and immunogenic, with no impairment of the response to the co-administered antigens.

REFERENCES

The Contents of which are Hereby Incorporated by Reference

[1] Vaccines. (eds. Plotkin & Orenstein). 4th edition, 2004, ISBN: 0-7216-9688-0.
[2] Dagan et al. (2004) *Infect Immun* 72:5383-91.
[3] Tejedor et al. (2004) *Pediatr Infect Dis J* 23:1109-15.
[4] Halperin et al. (2002) *Clin Invest Med* 25:243-51.
[5] Schmitt et al. (2003) *Vaccine* 21:3653-62.
[6] Shinefield et al. (1999) *Pediatr Infect Dis J.* 18:757-63.
[7] Slack et al. (2001) *J Infect Dis.* 184:1617-20.
[8] Tichmann-Schumann et al. (2005) *Pediatr Infect Dis* 24:70-77.
[9] WO02/00249.
[10] WO02/080965.
[1,1] Buttery et al. (2005) *JAMA* 293:1751-8.
[1,2] WO99/42130.
[1,3] Jones (2001) *Curr Opin Investig Drugs* 2:47-49.
[1,4] Costantino et al. (1992) *Vaccine* 10:691-8.
[1,5] Lieberman et al. (1996) *JAMA* 275:1499-503.
[1,6] WO02/058737.
[1,7] WO03/007985.
[1,8] Rennels et al. (2002) *Pediatr Infect Dis J* 21:978-979.
[1,9] Campbell et al. (2002) *J Infect Dis* 186:1848-1851.
[20] Arakere & Frasch (1991) *Infect. Immun.* 59:4349-4356.
[21] Michon et al. (2000) *Dev. Biol.* 103:151-160.
[22] Rubinstein & Stein (1998) *J. Immunol.* 141:4357-4362.
[23] WO2005/033148.
[24] WHO. Tech. Rep. Ser. 594:51, 1976.
[25] Watson (2000) *Pediatr Infect Dis J* 19:331-332.
[26] Rubin (2000) *Pediatr Clin North Am* 47:269-285, v.
[27] Jedrzejas (2001) *Microbiol Mol Biol Rev* 65:187-207.
[28] Zielen et al. (2000) *Infect. Immun.* 68:1435-1440.
[29] Darkes & Plosker (2002) *Paediatr Drugs* 4:609-630.

[30] WO98/51339.
[31] Rappuoli et al. (1991) *TIBTECH* 9:232-238.
[32] Module 6 of WHO's *The immunological basis for immunization series* (Robertson)
[33] Sesardic et al. (2001) *Biologicals* 29:107-22.
[34] NIBSC code: 98/560.
[35] Module 1 of WHO's *The immunological basis for immunization series* (Galazka).
[36] NIBSC code: 69/017.
[37] NIBSC code: DIFT.
[38] Sesardic et al. (2002) *Biologicals* 30:49-68.
[39] NIBSC code: 98/552.
[40] NIBSC code: TEFT.
[41] Vanlandschoot et al. (2005) *J Gen Virol* 86:323-31.
[42] European patent 0460716; U.S. Pat. No. 5,349,059.
[43] Crabeel et al. (1983) *Proc Natl Acad Sci USA* 78:5026-30.
[44] Cabezón et al. (1984) *Proc Natl Acad Sci USA* 81:6594-8.
[45] van der Straten et al. (1986) *DNA* 5:129-36.
[46] Harford et al. (1987) *Postgraduate Medical Journal* 63 (suppl 2):65-70.
[47] WO03/066094.
[48] WO93/24148.
[49] Ramsay et al. (2001) *Lancet* 357(9251):195-196.
[50] Lindberg (1999) *Vaccine* 17 Suppl 2:S28-36.
[51] Buttery & Moxon (2000) *J R Coll Physicians Lond* 34:163-168.
[52] Ahmad & Chapnick (1999) *Infect Dis Clin North Am* 13:113-133, vii.
[53] Goldblatt (1998) *J. Med. Microbiol.* 47:563-567.
[54] European patent 0477508.
[55] U.S. Pat. No. 5,306,492.
[56] WO98/42721.
[57] *Conjugate Vaccines* (eds. Cruse et al.) ISBN 3805549326, particularly vol. 10:48-114.
[58] Hermanson (1996) *Bioconjugate Techniques* ISBN: 0123423368 or 012342335X.
[59] WO96/40242.
[60] Nony et al. (2001) *Vaccine* 27:3645-51.
[61] *Vaccine Design: The Subunit and Adjuvant Approach* (eds. Powell & Newman) Plenum Press 1995 (ISBN 0-306-44867-X).
[62] U.S. Pat. No. 4,709,017.
[63] WO93/25210.
[64] U.S. Pat. No. 5,917,017.
[65] WO00/48638.
[66] Del Guidice et al. (1998) *Molecular Aspects of Medicine* 19:1-70.
[67] Anonymous (January 2002) *Research Disclosure*, 453077.
[68] Anderson (1983) *Infect Immun* 39(1):233-238.
[69] Anderson et al. (1985) *J Clin Invest* 76(1):52-59.
[70] EP-A-0372501.
[71] EP-A-0378881.
[72] EP-A-0427347.
[73] WO93/17712.
[74] WO94/03208.
[75] WO98/58668.
[76] EP-A-0471177.
[77] WO91/01146
[78] Falugi et al. (2001) *Eur J Immunol* 31:3816-3824.
[79] Baraldo et al. (2004) *Infect Immun* 72(8):4884-7.
[80] EP-A-0594610.
[81] Ruan et al. (1990) *J Immunol* 145:3379-3384.
[82] WO00/56360.
[83] Kuo et al. (1995) *Infect Immun* 63:2706-13.
[84] WO02/091998.
[85] WO01/72337.
[86] WO00/61761.
[87] Tejedor et al. (2006) *Pediatr Infect Dis J* 25:713-20.

---

The invention claimed is:

1. A kit, comprising a first immunogenic component and a second immunogenic component, wherein: (a) the first immunogenic component comprises an aqueous formulation of a diphtheria toxoid, a tetanus toxoid and acellular *B. pertussis* antigen; and (b) the second immunogenic component comprises a conjugated capsular saccharide from a OAc+ strain of *N. meningitidis* serogroup C and a conjugated *H. influenzae* type b antigen, in lyophilised form.

2. The kit of claim 1, wherein the OAc+ strain is of serotype 16.

3. The kit of claim 1, wherein the OAc+ strain is of serosubtype P1.7a,1 or serosubtype P1.1.

4. The kit of claim 1, wherein the OAc+ strain is a C:16:P1.7a,1 OAc+ strain.

5. The kit of claim 3, wherein the OAc+ strain is C11.

6. The kit of any one of claims 1 or 2-5, wherein the capsular saccharide from a OAc+ strain of *Neisseria meningitidis* serogroup C is conjugated to a CRM197 carrier protein, a tetanus toxoid carrier protein, a diphtheria toxoid carrier protein, or a *H. influenzae* protein D carrier protein.

7. The kit of claim 1, wherein the capsular saccharide from a OAc+ strain of *Neisseria meningitidis* serogroup C is a full length saccharide.

8. The kit of claim 1, wherein the capsular saccharide from a OAc+ strain of *Neisseria meningitidis* serogroup C is a fragment of a full length saccharide.

9. The kit of claim 1, wherein the capsular saccharide has a molecular weight of <100 kDa.

10. The kit of claim 8, wherein the capsular saccharide has a molecular weight of <100 kDa.

11. The kit of claim 9, wherein the capsular saccharide has a molecular weight of between 5 kDa-75 kDa.

12. The kit of claim 10, wherein the capsular saccharide has a molecular weight of between 5 kDa-75 kDa.

13. The kit of claim 1, wherein the conjugated capsular saccharide from a OAc+ strain of *Neisseria meningitidis* serogroup C has a saccharide:protein ratio (w/w) of between 1:10 and 10:1.

14. The kit of claim 1, wherein the conjugated capsular saccharide from a OAc+ strain of *N. meningitidis* serogroup C is adsorbed to an aluminium salt.

15. The kit of claim 1, wherein the conjugated capsular saccharide from a OAc+ strain of *N. meningitidis* serogroup C is not adsorbed to an aluminium salt.

16. The kit of claim 1, wherein the acellular *B. pertussis* antigen comprises one, two or three of the following antigens: (1) detoxified pertussis toxin ('PT'); (2) filamentous hemagglutinin ('FHA'); (3) pertactin.

17. The kit of claim 16, wherein PT, FHA and pertactin are adsorbed to aluminium hydroxide.

18. The kit of claim 1, wherein the diphtheria toxoid is adsorbed onto an aluminium hydroxide adjuvant.

19. The kit of claim 1, wherein the tetanus toxoid is adsorbed onto an aluminium hydroxide adjuvant.

20. The kit of claim 1, wherein the first component is a pentavalent diphtheria toxoid, a tetanus toxoid, acellular *B. pertussis* antigen, a hepatitis B virus surface antigen and an inactivated poliovirus antigen composition.

21. A kit comprising a first immunogenic component, a second immunogenic component, and a third immunogenic component, wherein: (a) the first immunogenic component comprises an aqueous formulation of a diphtheria toxoid, a tetanus toxoid and acellular *B. pertussis* antigen; and (b) the second immunogenic component comprises a conjugated capsular saccharide from a OAc+ strain of *N. meningitidis* serogroup C, in lyophilised form and (c) the third immunogenic component comprises saccharide antigens for at least *S. pneumoniae* serotypes 6B, 14, 19F and 23F.

22. The kit of claim 1, wherein: (a) the first immunogenic component comprises a diphtheria toxoid, a tetanus toxoid, an acellular *B. pertussis* antigen, a hepatitis B virus surface antigen and an inactivated poliovirus antigen; (b) the second immunogenic component comprises a conjugated capsular saccharide from *N. meningitidis* serogroup C, wherein the first immunogenic component is lyophilised and does not include an aluminium phosphate adjuvant.

23. The kit of claim 21, wherein the OAc+ strain is of serotype 16.

24. The kit of claim 21, wherein the OAc+ strain is of serosubtype P1.7a,1 or serosubtype P1.1.

25. The kit of claim 21, wherein the OAc+ strain is a C:16:P1.7a,1 OAc+ strain.

26. The kit of claim 21, wherein the OAc+ strain is C11.

27. The kit of claim 21, wherein the capsular saccharide from a OAc+ strain of *Neisseria meningitidis* serogroup C is conjugated to a CRM197 carrier protein, a tetanus toxoid carrier protein, a diphtheria toxoid carrier protein, or a *H. influenzae* protein D carrier protein.

28. The kit of claim 21, wherein the capsular saccharide from a OAc+ strain of *Neisseria meningitidis* serogroup C is a full length saccharide.

29. The kit of claim 21, wherein the capsular saccharide from a OAc+ strain of *Neisseria meningitidis* serogroup C is a fragment of a full length saccharide.

30. The kit of claim 21, wherein the capsular saccharide has a molecular weight of <100 kDa.

31. The kit of claim 29, wherein the capsular saccharide has a molecular weight of <100 kDa.

32. The kit of claim 30, wherein the capsular saccharide has a molecular weight of between 5 kDa-75 kDa.

33. The kit of claim 31, wherein the capsular saccharide has a molecular weight of between 5 kDa-75 kDa.

34. The kit of claim 21, wherein the conjugated capsular saccharide from a OAc+ strain of *Neisseria meningitidis* serogroup C has a saccharide:protein ratio (w/w) of between 1:10 and 10:1.

35. The kit of claim 21, wherein the conjugated capsular saccharide from a OAc+ strain of *N. meningitidis* serogroup C is adsorbed to an aluminium salt.

36. The kit of claim 21, wherein the conjugated capsular saccharide from a OAc+ strain of *N. meningitidis* serogroup C is not adsorbed to an aluminium salt.

37. The kit of claim 21, wherein the acellular *B. pertussis* antigen comprises one, two or three of the following antigens: (1) detoxified pertussis toxin ('PT'); (2) filamentous hemagglutinin ('FHA'); (3) pertactin.

38. The kit of claim 37, wherein PT, FHA and pertactin are adsorbed to aluminium hydroxide.

39. The kit of claim 21, wherein the diphtheria toxoid is adsorbed onto an aluminium hydroxide adjuvant.

40. The kit of claim 21, wherein the tetanus toxoid is adsorbed onto an aluminium hydroxide adjuvant.

* * * * *

SEQUENCE LISTING

```
<160> NUMBER OF SEQ ID NOS: 3

<210> SEQ ID NO 1
<211> LENGTH: 226
<212> TYPE: PRT
<213> ORGANISM: Hepatitis B virus

<400> SEQUENCE: 1

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Asn Thr Gly Pro Cys Lys Thr Cys Thr Thr Pro Ala
```

```
                    115                 120                 125
Gln Gly Asn Ser Met Phe Pro Ser Cys Cys Cys Thr Lys Pro Thr Asp
130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Ala Ile Trp Met Met Trp Tyr Trp Gly Pro Ser Leu Tyr Ser Ile
                195                 200                 205

Val Ser Pro Phe Ile Pro Leu Leu Pro Ile Phe Phe Cys Leu Trp Val
    210                 215                 220

Tyr Ile
225

<210> SEQ ID NO 2
<211> LENGTH: 1060
<212> TYPE: DNA
<213> ORGANISM: Saccharomyces cerevisiae

<400> SEQUENCE: 2
aagcttacca gttctcacac ggaacaccac taatggacac acattcgaaa tactttgacc      60 ctatttcga ggaccttgtc accttgagcc aagagagcc aagatttaaa ttttcctatg      120
acttgatgca aattcccaaa gctaataaca tgcaagacac gtacggtcaa gaagacatat    180
ttgacctctt aacaggttca gacgcgactg cctcatcagt aagacccgtt gaaaagaact    240
tacctgaaaa aaacgaatat atactagcgt tgaatgttag cgtcaacaac aagaagttta    300
ctgacgcgga ggccaaggca aaaagattcc ttgattacgt aagggagtta gaatcatttt    360
gaataaaaaa cacgcttttt cagttcgagt ttatcattat caatactgcc atttcaaaga    420
atacgtaaat aattaatagt agtgattttc ctaactttat ttagtcaaaa aattagcctt    480
ttaattctgc tgtaacccgt acatgcccaa aataggggc gggttacaca gaatatataa    540
catcgtaggt gtctgggtga acagtttatt cctggcatcc actaaatata atggagcccg    600 cttttttaagc tggcatccag aaaaaaaaag aatcccagca ccaaaatatt gttttcttca    660
ccaaccatca gttcataggt ccattctctt agcgcaacta cagagaacag gggcacaaac    720
aggcaaaaaa cgggcacaac ctcaatggag tgatgcaacc tgcctggagt aaatgatgac    780
acaaggcaat tgacccacgc atgtatctat ctcattttct tacaccttct attaccttct    840
gctctctctg atttggaaaa agctgaaaaa aaaggttgaa accagttccc tgaaattatt    900
cccctacttg actaataagt atataaagac ggtaggtatt gattgtaatt ctgtaaatct    960
atttcttaaa cttcttaaat tctacttta tagttagtct ttttttagt tttaaaacac      1020 caagaactta gtttcgaata acacacata aacaaacaaa                             1060

<210> SEQ ID NO 3
<211> LENGTH: 1063
<212> TYPE: DNA
<213> ORGANISM: Saccharomyces cerevisiae

<400> SEQUENCE: 3
aagcttacca gttctcacac ggaacaccac taatggacac acattcgaaa tactttgacc      60 ctatttcga ggaccttgtc accttgagcc aagagagcc aagatttaaa ttttcctatg      120
acttgatgca aattcccaaa gctaataaca tgcaagacac gtacggtcaa gaagacatat    180
```

-continued

```
ttgacctctt aacaggttca gacgcgactg cctcatcagt aagacccgtt gaaaagaact      240
tacctgaaaa aaacgaatat atactagcgt tgaatgttag cgtcaacaac aagaagttta      300
ctgacgcgga ggccaaggca aaaagattcc ttgattacgt aagggagtta gaatcatttt      360
gaataaaaaa cacgcttttt cagttcgagt ttatcattat caatactgcc atttcaaaga     420
atacgtaaat aattaatagt agtgattttc ctaactttat ttagtcaaaa aattagcctt     480
ttaattctgc tgtaacccgt acatgcccaa aataggggc gggttacaca gaatatataa     540
catcgtaggt gtctgggtga acagtttatt cctggcatcc actaaatata atggagcccg     600 cttttttaagc tggcatccag aaaaaaaaag aatcccagca ccaaaatatt gttttcttca     660
ccaaccatca gttcataggt ccattctctt agcgcaacta cagagaacag gggcacaaac     720
aggcaaaaaa cgggcacaac ctcaatggag tgatgcaacc tgcctggagt aaatgatgac     780
acaaggcaat tgacccacgc atgtatctat ctcattttct tacaccttct attaccttct     840
gctctctctg atttggaaaa agctgaaaaa aaaggttgaa accagttccc tgaaattatt     900
cccctacttg actaataagt atataaagac ggtaggtatt gattgtaatt ctgtaaatct     960
atttcttaaa cttcttaaat tctacttta tagttagtct ttttttagt tttaaaacac     1020 caagaactta gtttcgaata aacacacata aacaaacaaa atg                         1063
```